United States Patent
Dion

(10) Patent No.: US 8,588,924 B2
(45) Date of Patent: Nov. 19, 2013

(54) LOADED RF ANTENNA FOR IMPLANTABLE DEVICE

(75) Inventor: Philip G. Dion, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 541 days.

(21) Appl. No.: 12/397,187

(22) Filed: Mar. 3, 2009

(65) Prior Publication Data

US 2009/0228075 A1    Sep. 10, 2009

Related U.S. Application Data

(60) Provisional application No. 61/033,535, filed on Mar. 4, 2008, provisional application No. 61/088,986, filed on Aug. 14, 2008.

(51) Int. Cl.
*A61N 1/375* (2006.01)

(52) U.S. Cl.
USPC .......... 607/60; 607/1; 607/2; 607/32; 607/36; 343/718; 343/872; 343/873; 343/845

(58) Field of Classification Search
USPC .......... 607/30, 32, 60, 1, 2, 36; 343/895, 718, 343/872, 873, 845
See application file for complete search history.

(56) References Cited

U.S. PATENT DOCUMENTS

| | | | |
|---|---|---|---|
| 3,944,722 A | 3/1976 | Larsen | |
| 4,134,120 A | 1/1979 | DeLoach et al. | |
| 5,134,419 A | 7/1992 | Egashira | |
| 5,246,438 A | 9/1993 | Langberg | |
| 5,258,765 A | 11/1993 | Dörrie et al. | |
| 5,364,392 A * | 11/1994 | Warner et al. | 606/34 |
| 5,861,019 A | 1/1999 | Sun et al. | |
| 6,009,350 A | 12/1999 | Renken | |
| 6,115,636 A * | 9/2000 | Ryan | 607/60 |
| 6,167,312 A | 12/2000 | Goedeke | |
| 6,169,925 B1 | 1/2001 | Villaseca et al. | |
| 6,205,358 B1 | 3/2001 | Haeg et al. | |
| 6,320,545 B1 | 11/2001 | Nagumo et al. | |
| 6,456,256 B1 | 9/2002 | Amundson et al. | |

(Continued)

FOREIGN PATENT DOCUMENTS

| EP | 0505673 A1 | 9/1992 |
|---|---|---|
| EP | 1537895 A1 | 6/2005 |

(Continued)

OTHER PUBLICATIONS

"U.S. Appl. No. 09/798,249, Non-Final Office Action mailed Mar. 28, 2003", 7 pgs.

(Continued)

*Primary Examiner* — Allen Porter, Jr.
(74) *Attorney, Agent, or Firm* — Schwegman Lundberg & Woessner, P.A.

(57) ABSTRACT

This document discusses, among other things, a system and method for wirelessly transferring information electromagnetically at a first specified operating frequency range and at a second specified operating frequency range using an implantable antenna. In certain examples, the implantable antenna can include a first non-coiled segment and a first coiled segment, and the first specified operating frequency range and the second specified operating frequency range can be provided at least in part by a physical arrangement of the first coiled segment with respect to the first non-coiled segment.

16 Claims, 14 Drawing Sheets

(56) References Cited

U.S. PATENT DOCUMENTS

| | | | |
|---|---|---|---|
| 6,505,072 B1 | 1/2003 | Linder et al. | |
| 6,563,476 B1 | 5/2003 | Sheng-Gen et al. | |
| 6,574,510 B2 | 6/2003 | Von Arx et al. | |
| 6,614,406 B2 | 9/2003 | Amundson et al. | |
| 6,708,065 B2 | 3/2004 | Von Arx et al. | |
| 6,804,561 B2 | 10/2004 | Stover | |
| 6,809,701 B2 | 10/2004 | Amundson et al. | |
| 6,823,218 B2 * | 11/2004 | Berube | 607/156 |
| 6,868,288 B2 | 3/2005 | Thompson | |
| 6,888,514 B2 | 5/2005 | Sheng-Gen et al. | |
| 7,016,733 B2 | 3/2006 | Dublin et al. | |
| 7,047,076 B1 | 5/2006 | Li et al. | |
| 7,072,718 B2 | 7/2006 | Von Arx et al. | |
| 7,149,578 B2 | 12/2006 | Edvardsson | |
| 7,289,855 B2 | 10/2007 | Nghiem et al. | |
| 7,309,262 B2 | 12/2007 | Zart et al. | |
| 7,313,441 B2 | 12/2007 | Mass et al. | |
| 7,317,946 B2 | 1/2008 | Twetan et al. | |
| 7,319,901 B2 | 1/2008 | Dublin et al. | |
| 7,363,087 B2 | 4/2008 | Nghiem et al. | |
| 7,483,752 B2 | 1/2009 | Von Arx et al. | |
| 7,903,043 B2 | 3/2011 | Rawat et al. | |
| 8,170,680 B2 | 5/2012 | Ameri | |
| 2001/0034543 A1 | 10/2001 | Haeg | |
| 2002/0065539 A1 | 5/2002 | Von Arx et al. | |
| 2002/0095195 A1 | 7/2002 | Mass et al. | |
| 2002/0123776 A1 * | 9/2002 | Von Arx et al. | 607/60 |
| 2002/0190916 A1 * | 12/2002 | Makino | 343/895 |
| 2003/0014091 A1 * | 1/2003 | Rastegar et al. | 607/61 |
| 2003/0018246 A1 | 1/2003 | Govari et al. | |
| 2003/0025645 A1 | 2/2003 | Amundson et al. | |
| 2003/0114897 A1 * | 6/2003 | Von Arx et al. | 607/60 |
| 2003/0117340 A1 | 6/2003 | Sheng-Gen et al. | |
| 2003/0195589 A1 | 10/2003 | Von Arx et al. | |
| 2004/0027306 A1 | 2/2004 | Amundson et al. | |
| 2004/0095289 A1 * | 5/2004 | Bae et al. | 343/895 |
| 2004/0176811 A1 | 9/2004 | Von Arx et al. | |
| 2005/0113886 A1 | 5/2005 | Fischell et al. | |
| 2005/0134520 A1 | 6/2005 | Rawat et al. | |
| 2005/0203583 A1 | 9/2005 | Twetan et al. | |
| 2005/0203584 A1 | 9/2005 | Twetan et al. | |
| 2005/0222633 A1 | 10/2005 | Edvardsson | |
| 2006/0089682 A1 | 4/2006 | Kronich et al. | |
| 2006/0095093 A1 | 5/2006 | Bettesh et al. | |
| 2006/0224206 A1 * | 10/2006 | Dublin et al. | 607/37 |
| 2006/0247711 A1 | 11/2006 | Verhoef et al. | |
| 2006/0247712 A1 | 11/2006 | Fuller et al. | |
| 2006/0287693 A1 * | 12/2006 | Kraft et al. | 607/60 |
| 2007/0119741 A1 | 5/2007 | Wenger et al. | |
| 2007/0142829 A1 | 6/2007 | Ahn et al. | |
| 2007/0179554 A1 | 8/2007 | Iyer et al. | |
| 2007/0222697 A1 | 9/2007 | Caimi et al. | |
| 2007/0260294 A1 | 11/2007 | Schulman et al. | |
| 2007/0288065 A1 | 12/2007 | Christman et al. | |
| 2007/0288066 A1 | 12/2007 | Christman et al. | |
| 2008/0021522 A1 | 1/2008 | Verhoef et al. | |
| 2008/0039898 A1 | 2/2008 | Lim et al. | |
| 2009/0192574 A1 | 7/2009 | Von Arx et al. | |
| 2009/0228074 A1 | 9/2009 | Edgell et al. | |
| 2009/0228076 A1 | 9/2009 | Ameri | |

FOREIGN PATENT DOCUMENTS

| | | | |
|---|---|---|---|
| EP | 1362614 B1 | 3/2008 | |
| JP | 3-003824 A | 1/1991 | |
| JP | 3159402 A | 7/1991 | |
| JP | 200059130 A | 2/2000 | |
| JP | 2001068917 | 3/2001 | |
| JP | 2004080713 | 3/2004 | |
| JP | 2004193774 A | 7/2004 | |
| JP | 2006130322 A | 5/2006 | |
| JP | 5054205 B2 | 10/2012 | |
| WO | WO-98/48895 A1 | 11/1998 | |
| WO | WO-0016439 | 3/2000 | |
| WO | WO-0066220 A1 | 11/2000 | |
| WO | WO-02/31909 A1 | 4/2002 | |
| WO | WO-03/053515 A1 | 7/2003 | |
| WO | WO-2005/123186 A1 | 12/2005 | |
| WO | WO-2005123186 A1 | 12/2005 | |
| WO | WO-2006060750 A1 | 6/2006 | |
| WO | WO-2006104847 A1 | 10/2006 | |
| WO | WO-2006131302 A1 | 12/2006 | |
| WO | WO-2009/111009 A1 | 9/2009 | |
| WO | WO-2009/111012 A1 | 9/2009 | |

OTHER PUBLICATIONS

"U.S. Appl. No. 09/798,249, Notice of Allowance mailed Oct. 21, 2003", 5 pgs.

"U.S. Appl. No. 09/798,249, Response filed Jul. 28, 2003 to Non Final Office Action mailed Mar. 28, 2003", 8 pgs.

"U.S. Appl. No. 10/800,596, Final Office Action mailed Dec. 4, 2007", 4 pgs.

"U.S. Appl. No. 10/800,596, Response filed Feb. 4, 2008 to Final Office Action mailed Dec. 4, 2007", 6 pgs.

"U.S. Appl. No. 10/800,596, Amendment and Response filed Jun. 7, 2007 to Final Office Action mailed Mar. 7, 2007", 8 pgs.

"U.S. Appl. No. 10/800,596, Final Office Action mailed Mar. 7, 2007", 7 pgs.

"U.S. Appl. No. 10/800,596, Non-Final Office Action mailed Jun. 28, 2007", 6 pgs.

"U.S. Appl. No. 10/800,596, Response filed Jun. 3, 2008 to Non-Final Office Action mailed Mar. 3, 2008", 8 pgs.

"U.S. Appl. No. 10/800,596, Response filed Sep. 28, 2007 to Non-Final Office Action mailed Jun. 28, 2007", 8 pgs.

"U.S. Appl. No. 10/800,596, Non-Final Office Action mailed Mar. 3, 2008", 9 pgs.

"International Application Serial No. PCT/US2009/001349, International Search Report mailed May 20, 2009", 5 pgs.

"International Application Serial No. PCT/US2009/001349, Written Opinion mailed May 20, 2009", 7 pgs.

"International Application Serial No. PCT/US2009/001354, International Search Report mailed May 20, 2009", 5 pgs.

"International Application Serial No. PCT/US2009/001354, Written Opinion mailed May 20, 2009", 7 pgs.

Basset, P., et al., ""Chip-Size" Antennas for Implantable Sensors and Smart Dust", *The 13th International Conference on Solid-State Sensors, Actuators and Microsystems. Digest of Technical Papers. Transducers '05*, (Seoul, Korea, Jun. 5-9, 2005), 457-460.

Gosalia, K., et al., "Investigation of a Microwave Data Telemetry Link for a Retinal Prosthesis", *IEEE Transactions on Microwave Theory and Techniques*, 52(8), (2004), 1925-1933.

Gosalia, K., "Novel Compact Antennas for Biomedical Implants and Wireless Applications", *Dissertation, PhD, Electrical Engineering*, Graduate and Wireless Faculty of North.Carolina State University, (2004), 172 pgs.

Jacobsen, S., et al., "Characteristics of Microstrip Muscle-Loaded Single-Arm Archimedean Spiral Antennas as Investigated by FDTD Numerical Computations", *IEEE Transactions on Biomedical Engineering*, 52(2), (2005), 321-330.

Johansson, A. J., "Performance Measures of Implant Antennas", *First European Conference on Antennas and Propagation (EuCAP 2006)*, (Nice, France, Nov. 6-10, 2006), 1-4.

Karacolak, T., et al., "Design of a Dual-Band Implantable Antenna and Development of Skin Mimicking Gels for Continuous Glucose Monitoring", *IEEE Transactions on Microwave Theory and Techniques*, 56(4), (Apr. 2008), 1001-1008.

Kim, J., et al., "An Implanted Antenna in the Spherical Human Head: SAR and Communication Link Performance", *IEEE Topical Conference on Wireless Communication Technology*, (2003), 202-203.

Kim, J., et al., "Implanted Antennas Inside a Human Body: Simulations, Designs, and Characterizations", *IEEE Transactions on Microwave Theory and Techniques*, 52(8), (2004), 1934-1943.

Ma, L., et al., "A Wearable Flexible Multi-Band Antenna Based on a Square Slotted Printed Monopole", *2008 Loughborough Antennas & Propagation Conference (LAPC 2008)*, (Mar. 17-18, 2008, Loughborough, United Kingdom), 345-348.

(56) References Cited

OTHER PUBLICATIONS

Neirynck, D., et al., "Exploiting Multiple-Input Multiple-Output in the Personal Sphere", *IEt Microwaves Antennas & Propagation*, 1(6), 2007, 1170-1176.

"U.S. Appl. No. 12/397,180, Notice of Allowance mailed Jun. 14, 2011", 8 pgs.

"U.S. Appl. No. 12/397,199, Non-Final Office Action mailed Apr. 21, 2011", 8 pgs.

"U.S. Appl. No. 12/397,199, Response filed Jul. 19, 2011 to Non-Final Office Action mailed Apr. 21, 2011", 12 pgs.

"U.S. Appl. No. 12/397,199, Notice of Allowance mailed Jan. 5, 2012", 8 pgs.

"U.S. Appl. No. 12/397,199, Notice of Allowance mailed Sep. 23, 2011", 9 pgs.

"Japanese Application Serial No. 2010-548748, Office Action mailed Oct. 4, 2011", (w/ English Translation), 5 pgs.

"Japanese Application Serial No. 2010-549652, Office Action mailed Oct. 4, 2011", (w/ English Translation), 6 pgs.

"Australian Application Serial No. 2009220201, Response filed Oct. 12, 2012 to First Examiners Report mailed Mar. 28, 2012", 5 pgs.

"European Application Serial No. 09716210.1, Office Action mailed Nov. 4, 2010", 1 pg.

"European Application Serial No. 09716210.1, Response filed Dec. 13, 2010 to Office Action mailed Nov. 4, 2010", 17 pgs.

"European Application Serial No. 09717702.6, Office Action mailed Oct. 21, 2010", 2 pgs.

"European Application Serial No. 09717702.6, Response filed Nov. 30, 2010 to Office Action mailed Oct. 21, 2010", 15 pgs.

"International Application Serial No. PCT/US2009/001349, International Preliminary Report on Patentability mailed Sep. 16, 2010", 8 pgs.

"International Application Serial No. PCT/US2009/001354, International Preliminary Report on Patentability mailed Sep. 16, 2010", 8 pgs.

"Australian Application No. 2009220201, Examination Report No. 2, Dated Oct. 23, 2012", 3 pgs.

"Australian Application Serial No. 2009220201, Subsequent Examiner Report mailed Jan. 3, 2013", 3 pgs.

"Australian Patent Application No. 2009220198, Response Filed Nov. 1, 2012", 2 pgs.

"European Application Serial No. 09716210.1, Office Action mailed Jan. 28, 2013", 6 pgs.

"European Application Serial No. 09717702.6, Office Action mailed Feb. 28, 2013", 6 pgs.

"Japanese Application Serial No. 2010-548748, Response filed Oct. 31, 2012 to Office Action mailed Jul. 3, 2012", With English Translation, 10 pgs.

"Australian Application Serial No. 2009220201, First Examiners Report mailed Mar. 28, 2012", 2 pgs.

"Japanese Application Serial No. 2010-548748, Office Action mailed Jul. 3, 2012", 6 pgs.

"Japanese Application Serial No. 2010-548748, Response filed Apr. 4, 2012 to Office Action mailed Oct. 4, 2011", With English Claims, 11 pgs.

"Japanese Application Serial No. 2010-549652, Response filed Apr. 4, 2012 to Office Action mailed Oct. 4, 2011", (w/ English Translation of Amended Claims), 8 pgs.

* cited by examiner

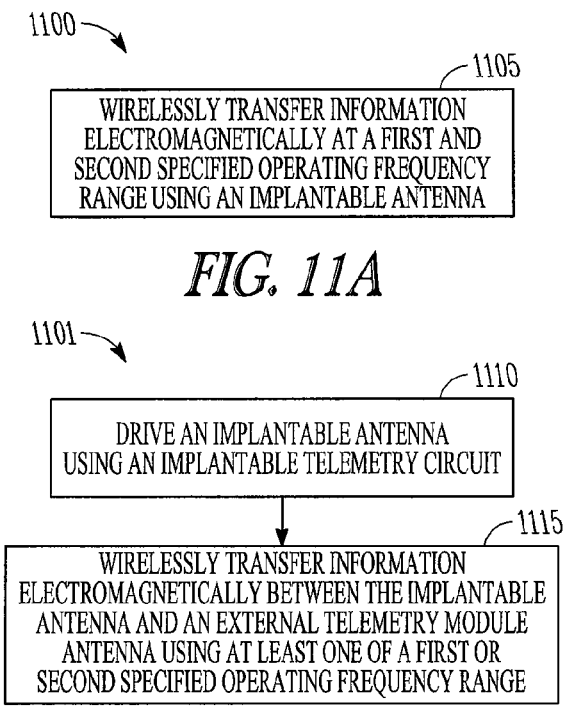
FIG. 11A
FIG. 11B
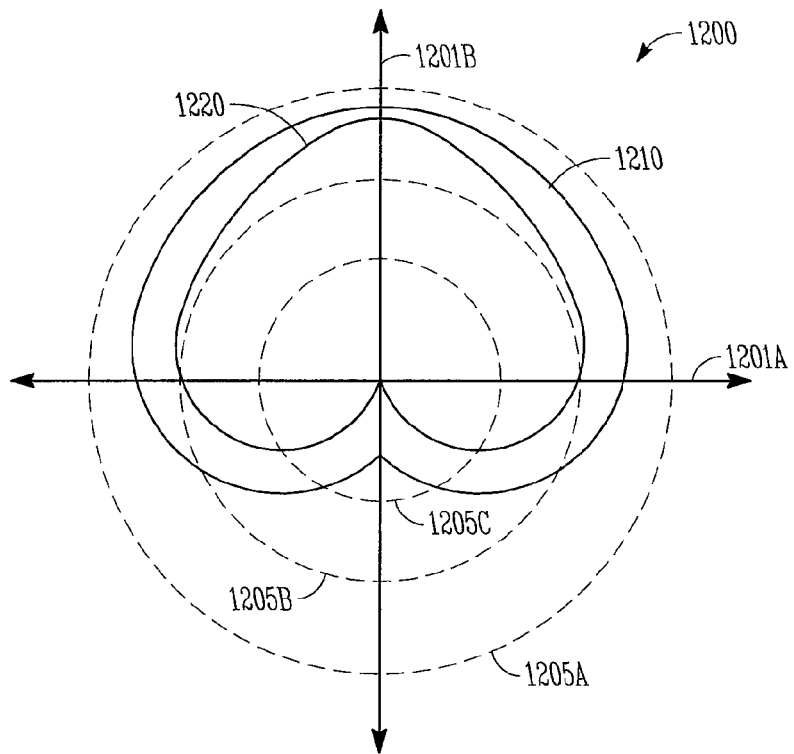
FIG. 12

LOADED RF ANTENNA FOR IMPLANTABLE DEVICE

CROSS REFERENCE TO RELATED APPLICATIONS

This patent application claims the benefit of priority, under 35 U.S.C. Section 119(e), to Greg Carpenter et al., U.S. Provisional Patent Application Ser. No. 61/033,535, entitled "ANTENNA FOR IMPLANTABLE MEDICAL DEVICE," filed on Mar. 4, 2008, incorporated herein by reference in its entirety.

This patent application also claims the benefit of priority, under 35 U.S.C. Section 119(e), to Phil Dion, U.S. Provisional Patent Application Ser. No. 61/088,986, entitled "LOADED RF ANTENNA FOR IMPLANTABLE DEVICE," filed on Aug. 14, 2008, incorporated herein by reference in its entirety.

BACKGROUND

Medical devices can be implanted in a body to perform tasks including monitoring, detecting, or sensing physiological information in or otherwise associated with the body, diagnosing a physiological condition or disease, treating or providing a therapy for a physiological condition or disease, or restoring or otherwise altering the function of an organ or a tissue. Examples of an implantable medical device can include a cardiac rhythm management device, such as a pacemaker, a cardiac resynchronization therapy device, a cardioverter or defibrillator, a neurological stimulator, a neuromuscular stimulator, or a drug delivery system. In certain examples, the implantable medical device can include a telemetry circuit and an antenna, coupled to the telemetry circuit, the combination of which can be configured to provide wireless communication between the implantable medical device and an external device, e.g., to send information (such as physiological or other information) from the implantable medical device to the external device, or to receive information (e.g., such as programming instructions) at the implantable medical device from the external device.

Magnetic coupling can be used to provide short-range (e.g., a few centimeters) communication between an implantable medical device implanted in a body and an external device, or between an implantable medical device outside of the body and an external device. However, magnetic coupling communication largely relies on near-field radiation, where the field distribution is highly dependent upon the distance from, and orientation of, the antenna, which grossly limits the effective range of wireless communication between the implantable medical device and the external device.

As an alternative to magnetic coupling, or in addition to magnetic coupling, low power radio frequency (RF) communication, having an extended range over magnetic coupling, can be used to provide communication between an implantable medical device and an external device. However, many RF communication channels, bands, or frequencies are limited by governing bodies or other regulatory agencies, such as the Federal Communications Commission (FCC) or other regulatory body. As such, a frequency available for use in one area may not be available for use in another area.

Further, a desired antenna length can be dependent on the specified transmission frequency. For certain frequencies, the desired antenna length can be difficult to contain within a medical device.

OVERVIEW

The present inventor has recognized, among other things, a system or method for wirelessly transferring information electromagnetically at a first specified operating frequency range and at a second specified operating frequency range using an implantable antenna. In certain examples, the implantable antenna can include a first non-coiled segment and a first coiled segment, and the first specified operating frequency range and the second specified operating frequency range can be provided at least in part by a physical arrangement of the first coiled segment with respect to the first non-coiled segment.

In Example 1, a system includes an implantable telemetry circuit, an implantable antenna electrically connected to the implantable telemetry circuit, the implantable antenna comprising a first non-coiled segment and a first coiled segment attached to the first non-coiled segment, and wherein the implantable antenna is configured to wirelessly transfer information electromagnetically using a first specified operating frequency range and a second specified operating frequency range, and wherein the first specified operating frequency range and the second specified operating frequency range are provided at least in part by a physical arrangement of the first coiled segment with respect to the first non-coiled segment.

In Example 2, the implantable antenna of Example 1 optionally includes a second non-coiled segment attached to the first coiled segment, and the first and second specified operating frequency ranges of Example 1 are optionally provided at least in part by a physical arrangement of the second non-coiled segment with respect to the first coiled segment, and with respect to the first non-coiled segment.

In Example 3, the implantable antenna of any one or more of Examples 1-2 optionally includes a second coiled segment attached to the second non-coiled segment, wherein the second non-coiled segment is located between the second coiled segment and the first coiled segment, the first specified operating frequency range and the second specified operating frequency range of Examples 1-2 are optionally provided at least in part by a physical arrangement of the second coiled segment with respect to the first coiled segment, the first non-coiled segment, and the second non-coiled segment.

In Example 4, a first mid-band frequency, centered in the first specified operating frequency range, of any one or more of Examples 1-3 is optionally offset from a second mid-band frequency, centered in the second operating frequency range, by at least an octave.

In Example 5, the first and second specified operating frequency ranges of any one or more of Examples 1-4 are optionally selected from a list including at least one of:
  (1) a Medical Implant Communications Service (MICS) band range extending from approximately 402 MHz. to approximately 405 MHz.;
  (2) a Short Range Device (SRD) band range extending from approximately 862 MHz. to approximately 870 MHz.;
  (3) a first Industrial-Scientific-Medical (ISM) band range extending from approximately 902 MHz. to approximately 928 MHz.; or
  (4) a second ISM band range extending from approximately 2400 MHz. to approximately 2500 MHz.

In Example 6, a longest linear physical dimension of the implantable antenna of any one or more of Examples 1-5 is optionally less than or equal to a quarter of a longest specified operating wavelength of the implantable antenna in a biological medium.

In Example 7, the implantable antenna of any one or more of Examples 1-6 optionally exhibits a higher radiation efficiency in at least one of the first and second operating frequency ranges than would be obtained when the first coiled segment is replaced by a similar length non-coiled segment.

In Example 8, the physical arrangement of the first coiled segment with respect to the first non-coiled segment of any one or more of Examples 1-7 is optionally configured such that the implantable antenna in a biological medium approximates a conjugate match to an output impedance of the implantable telemetry circuit for at least one of the first and second operating frequency ranges.

In Example 9, the implantable telemetry circuit of any one or more of Examples 1-8 optionally includes an impedance matching element, connected to the implantable antenna, and wherein the first coiled segment is configured to inductively load the implantable telemetry circuit without requiring the matching element to include a discrete inductor.

In Example 10, the implantable antenna of any one or more of Examples 1-9 optionally exhibits less directivity in at least one of the first and second operating frequency ranges than would be obtained when the first coiled segment is replaced by a similar length non-coiled segment.

In Example 11, the system of any one or more of Examples 1-10 optionally includes an implantable housing sized and shaped for implant within a human or animal body, the implantable housing comprising a conductive material and containing at least a portion of the implantable telemetry circuit, wherein the conductive material is electrically connected to the implantable telemetry circuit, and an implantable dielectric compartment sized and shaped for implant within a human or animal body, the implantable dielectric compartment containing at least a portion of the implantable antenna, and wherein the implantable dielectric compartment is coupled to the housing.

In Example 12, the system of any one or more of Examples 1-11 optionally includes an external telemetry module comprising an external antenna and an external telemetry circuit electrically connected to the external antenna, wherein the implantable antenna and the external antenna are wirelessly coupled, and wherein the external antenna is configured to wirelessly transfer information electromagnetically between the implantable medical assembly and the external telemetry module using at least one of the first or second specified operating frequency ranges.

In Example 13, a longest linear dimension of the first coiled segment of any one or more of Examples 1-12 is optionally shorter than or equal to a longest linear dimension of the first non-coiled segment.

In Example 14, a method includes wirelessly transferring information electromagnetically at a first specified operating frequency range and at a second specified operating frequency range using an implantable antenna, the implantable antenna comprising a first non-coiled segment and a first coiled segment attached to the first non-coiled segment, and wherein the first specified operating frequency range and the second specified operating frequency range are provided at least in part by a physical arrangement of the first coiled segment with respect to the first non-coiled segment.

In Example 15, the implantable antenna of Example 14 optionally comprises a second non-coiled segment attached to the first coiled segment, wherein the wirelessly transferring information electromagnetically using the implantable antenna includes using the second non-coiled segment, and wherein the first specified operating frequency range and the second specified operating frequency range are provided at least in part by a physical arrangement of the second non-coiled segment with respect to the first coiled segment and the first non-coiled segment.

In Example 16, the implantable antenna of any one or more of Examples 14-15 optionally comprises a second coiled segment located between the second coiled segment and the first coiled segment, wherein the wirelessly transferring information electromagnetically using the implantable antenna includes using the second coiled segment, and wherein the first specified operating frequency range and the second specified operating frequency range are provided at least in part by a physical arrangement of the second coiled segment with respect to the first coiled segment, the first non-coiled segment, and the second non-coiled segment.

In Example 17, the wirelessly transferring information electromagnetically of any one or more of Examples 14-16 optionally includes using the first specified operating frequency range having a first mid-band frequency, and wherein the first mid-band frequency is offset from a second mid-band frequency by at least an octave.

In Example 18, the wirelessly transferring information electromagnetically of any one or more of Examples 14-17 optionally includes using an implantable antenna having a longest linear dimension of the first coiled segment shorter than or equal to a longest linear dimension of the first non-coiled segment.

In Example 19, the method of any one or more of Examples 14-18 optionally includes substantially matching a conjugate impedance of the implantable antenna in a biological medium using the implantable telemetry circuit.

In Example 20, the substantially matching of any one or more of Examples 14-19 optionally includes inductively loading the implantable telemetry circuit using the coiled segment.

In Example 21, the method of any one or more of Examples 14-20 optionally includes driving the implantable antenna using the implantable telemetry circuit, wherein the implantable telemetry circuit is contained within an implantable conductive housing, and wherein the antenna is located outside of the conductive housing, and wherein the wirelessly transferring information electromagnetically of any one or more of Examples 14-20 optionally includes wirelessly transferring information electromagnetically between the implantable antenna and an external telemetry module antenna using at least one of the first specified operating frequency range or the second specified operating frequency range.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 11A-B illustrate generally examples of a process including wirelessly transferring information using an implantable antenna.

FIG. 12 illustrates generally an example of a comparison between a normalized radiation pattern in a plane of an antenna with a coiled segment versus a similar radiation pattern of an antenna without a coiled segment.

DETAILED DESCRIPTION

The present inventor has recognized, among other things, an implantable antenna, including a coiled segment and a non-coiled segment, which can appear electrically longer than its actual physical length, thereby allowing the antenna to be physically shorter for a desired transmission frequency. In an example, the implantable antenna disclosed herein can allow a physical antenna length shorter than one quarter of a desired operating wavelength relative to the desired transmission frequency. In other examples, the implantable antenna disclosed herein can be used to match an radio frequency (RF) output of a transmitter, receiver, or transceiver external to an implantable medical device (IMD) coupled to or containing the implantable antenna. Further, the present inventor has recognized, among other things, an implantable antenna, including a coiled segment and a non-coiled segment, capable of operating in more than one desired frequency range. In certain examples, reducing the physical length of the implantable antenna or operating in more than one desired frequency range can reduce an IMD assembly complexity (e.g., size, cost, component count, etc.) or provide operating capability in multiple geographies in compliance with local spectrum utilization rules. In other examples, the operation in more than one desired frequency range can provide backup wireless capability if a particular frequency range is unavailable (e.g., due to interference, poor propagation characteristics, malfunction, high data error rate, etc.).

Figure 1:
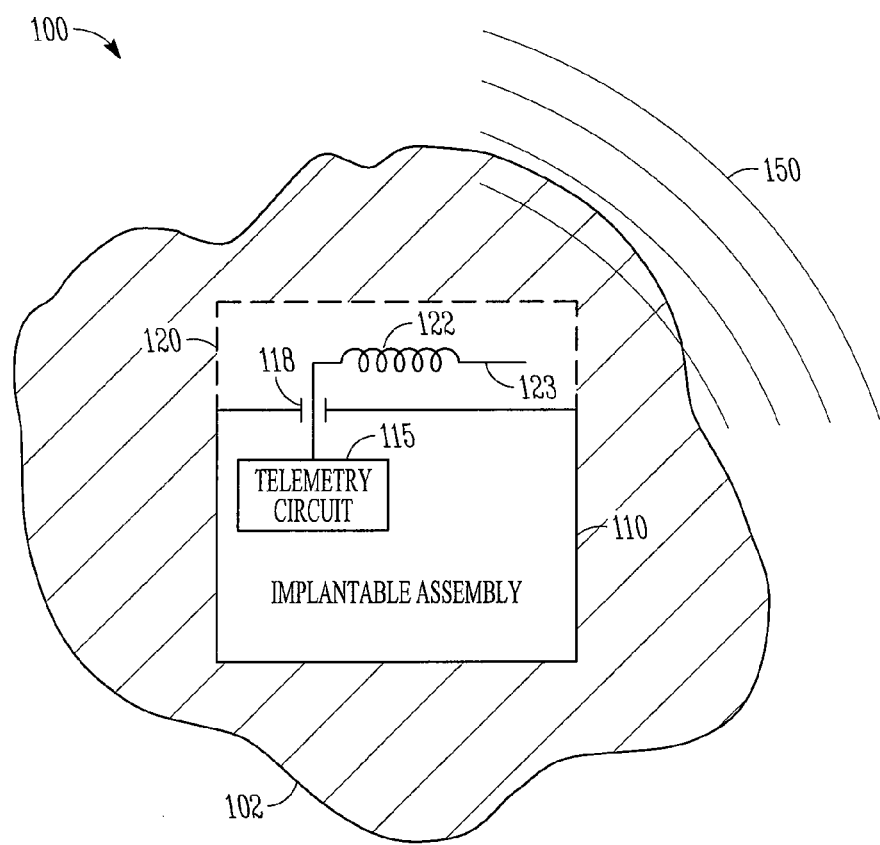
FIG. 1 illustrates generally an example of a system including an implantable telemetry circuit and an implantable antenna.

FIG. 1 illustrates generally an example of a system 100 including an implantable telemetry circuit 115 and an implantable antenna 120. In an example, the system 100 can include an implantable assembly housing 110 configured to house at least a portion of an implantable telemetry circuit 115. In an example, the housing 110 can be made of a conductive biocompatible material, such as titanium. In certain examples, the implantable antenna 120 can be driven by the telemetry circuit 115 via a feed-through 118 through the housing 110. In an example, the feed-through 118 can prevent the housing 110 from attenuating, shorting out, or otherwise altering the radiation of electromagnetic energy 150 by the antenna 120.

In an example, the implantable antenna 120 can include a coiled segment 122 and a non-coiled segment 123 configured to radiate electromagnetic energy 150 or to receive radiated electromagnetic energy 150 over one or more specified frequency ranges.

In an example, the implantable antenna 120 can be configured to radiate electromagnetic energy 150 or to receive radiated electromagnetic energy 150 when substantially surrounded by an implant medium 102. In certain examples, the implant medium 102 can include a biological medium, such as bodily fluid, skin tissue, fat tissue, muscle tissue, organ tissue, bone, or other biological medium. In an example, the implant medium can include a portion of a human or a portion of an animal (e.g., an IMD can be used as a monitoring or therapy delivery device for pets, livestock, etc.)

Figure 2:
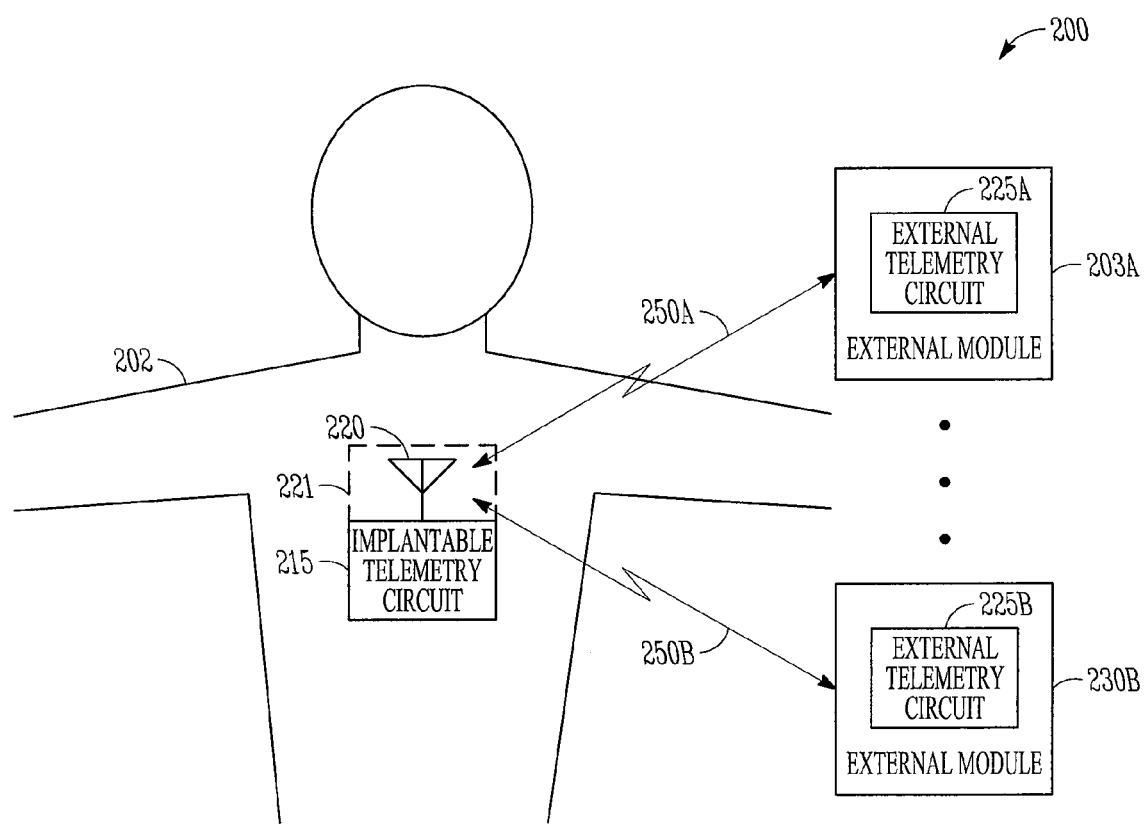
FIG. 2 illustrates generally an example of a system including an implantable telemetry circuit and an implantable telemetry antenna in communication with one or more external modules.

FIG. 2 illustrates generally an example of a system 200 including an implantable telemetry circuit 215 and an implantable telemetry antenna 220 in communication, such as in RF wireless communication (e.g., using a first RF wireless communication link 250A, a second RF wireless communication link 250B, etc.), with one or more external modules, such as a first external module 230A, a second external module 230B, etc. In an example, the implantable telemetry circuit 215 and the implantable telemetry antenna 220 can be implanted within a patient 202, e.g., subcutaneously, intramuscularly, intrathoracically, or otherwise implanted within the patient 202. In an example, the implantable antenna 220 can be at least partially surrounded by a dielectric compartment 221 comprising a biocompatible dielectric material (e.g., the implantable antenna 220 can be inserted into a cavity within the compartment 221, or the compartment 221 can be formed at least in part by overmolding the antenna 220).

In an example, the first external module 230A or the second external module 230B can include an external telemetry circuit, e.g., a first external telemetry circuit 225A or a second external telemetry circuit 225B, respectively. In certain examples, the first RF wireless communication link 250A can be accomplished using a first range of RF operating frequencies, and the second RF wireless communication link 250B can be accomplished using a second range of RF operating frequencies different than the first range of operating frequencies. In other examples, the first external telemetry circuit 225A or the second external telemetry circuit 225B can use either a first or second operating range of frequencies, or both, for wireless communication. In certain examples, the first external telemetry circuit 225A or the second external telemetry circuit 225B can be electrically connected to one or more external antennas.

Figure 3:
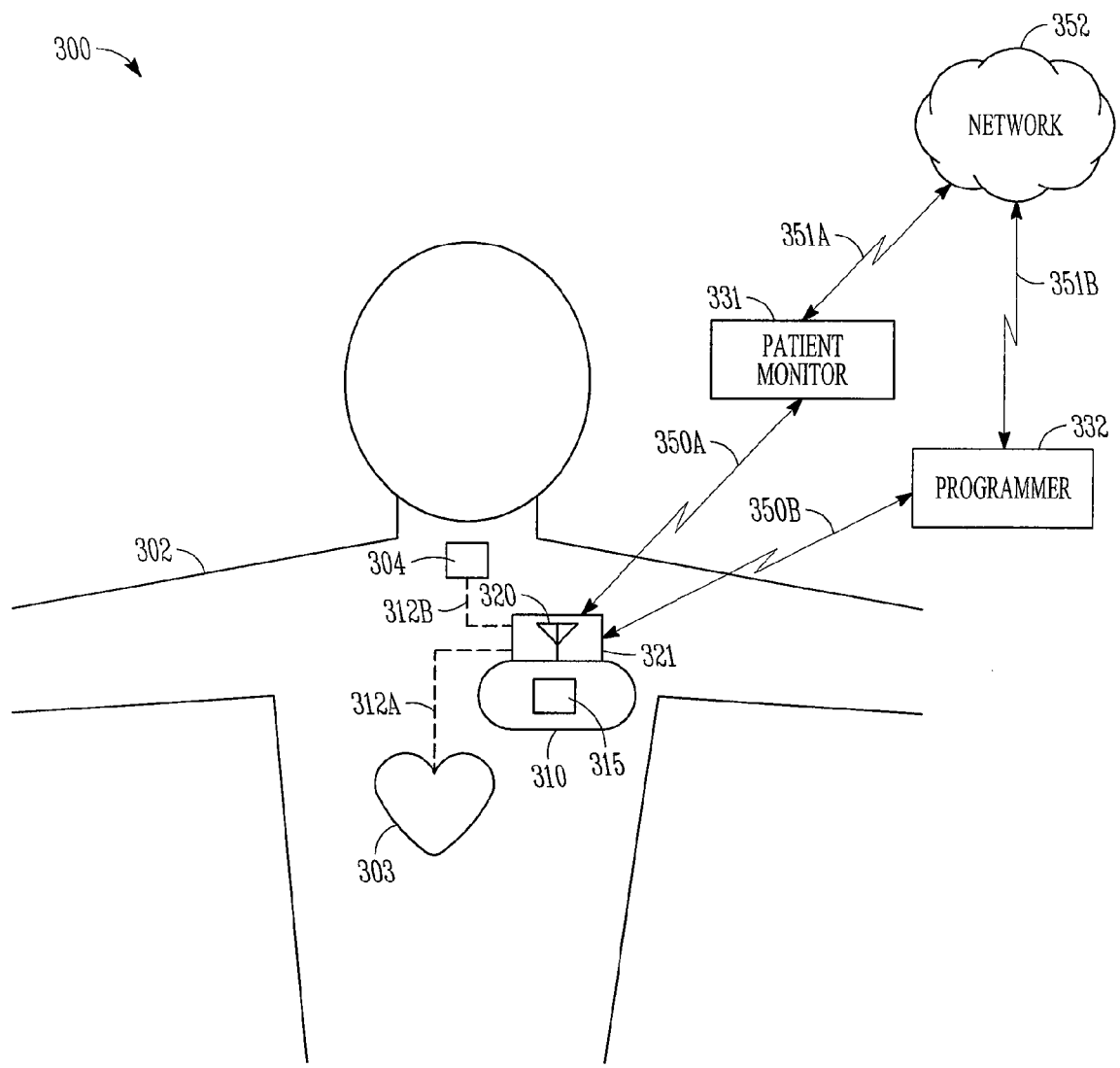
FIG. 3 illustrates generally an example of a system including an implantable medical device (IMD) in communication with at least one of a patient monitor or a programmer.

FIG. 3 illustrates generally an example of a system 300 including an implantable medical device (IMD) 310 in communication, such as in RF wireless communication (e.g., using a first RF wireless communication link 350A, a second RF wireless communication link 350B, etc.), with at least one of a patient monitor 331 or a programmer 332.

In the example of FIG. 3, the IMD 310 can include an implantable telemetry circuit 315 electrically connected to an implantable antenna 320. As similarly discussed with respect to FIG. 2, in some examples, the first RF wireless communication link 350A or the second RF wireless communication link 350B can use more than one RF operating frequency range. In such examples, a single implantable antenna 320 can be configured to operate at two or more RF wireless operating frequencies to support the first RF wireless communication link 350A or the second RF wireless communication link 350B.

According to the example of FIG. 3, the implantable antenna 320 can be at least partially surrounded by a connector block 321. In certain examples, the connector block 321 can be at least partially made of a dielectric material. In various examples, the connector block 321 can also provide an electrical or mechanical connection between the IMD 310 and one or more implantable leads, e.g., a first implantable lead 312A or a second implantable lead 312B. In some examples, the first implantable lead 312A or the second implantable lead 312B can be routed within a patient body 302 to various sites, e.g., to provide a physiologic monitoring of an electrical or a mechanical signal, or to provide a therapy, such as an electrostimulus therapy, a targeted drug release, or other therapy. In the example of FIG. 3, the first implantable lead 312A can be routed to a cardiac tissue site 303 (e.g., an endocardial site, an epicardial site, a site within the myocardium, or other cardiac tissue site) to deliver a therapy, such as a cardiac rhythm management therapy, or the second implantable lead 312B can be routed to a neural target 304 (e.g., a vagal nerve or other neural target) to deliver a therapy, such as a neural stimulation therapy.

In certain examples, the patient monitor 331, the programmer 332, or both the patient monitor 331 and the programmer 332 can be communicatively coupled, e.g., using a first coupling 351A or a second coupling 351B, with a network 352. In an example, the first coupling 351A or the second coupling 351B can include a wired coupling or a wireless coupling. In an example, information can be wirelessly transferred from the IMD 310 to the patient monitor 331 or the programmer 332, and then transferred from the patient monitor 331 or the programmer 332 to the network 352 using the first coupling 351A or using the second coupling 351B.

Figure 4:
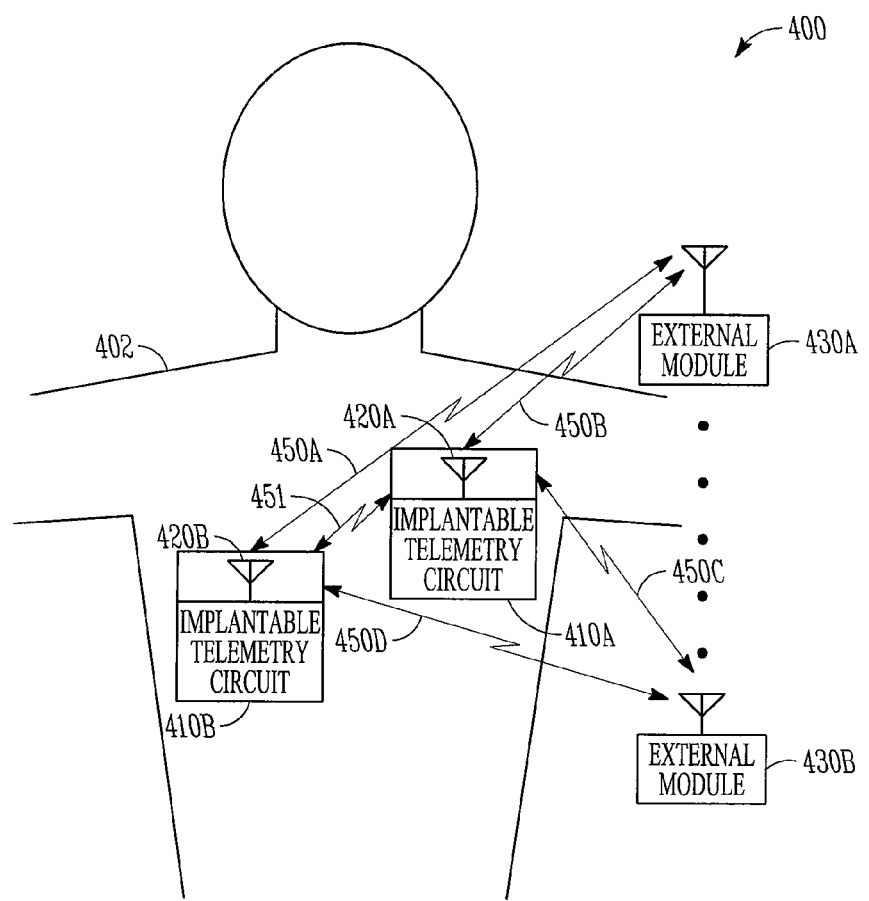
FIG. 4 illustrates generally an example of a system including two or more implantable telemetry circuits in communication with each other, or in communication with one or more external modules.

FIG. 4 illustrates generally an example of a system 400 including two or more implantable telemetry circuits, such as a first implantable telemetry circuit 410A, a second implantable telemetry circuit 410B, etc., in communication, such as in RF wireless communication (e.g., using a RF wireless communication link 451), with each other, or in communication, such as in RF wireless communication (e.g., using a first RF wireless communication link 450A, a second RF wireless communication link 450B, etc.), with one or more external modules, such as a first external module 430A, a second external module 430B, etc.

In an example, the first implantable telemetry circuit 410A or the second implantable telemetry circuit 410B can use the same RF wireless communication scheme for wirelessly coupling to each other (e.g., using the RF wireless communication link 451) as can be used for wirelessly coupling to an external module (e.g., using the first RF wireless communication link 450A or the second RF wireless communication link 450B). In other examples, the first implantable telemetry circuit 410A or the second implantable telemetry circuit 410B can use a first RF wireless operating frequency range for wirelessly coupling to each other (e.g., using the RF wireless communication link 451), and a second RF wireless operating frequency range for wirelessly coupling to an external module (e.g., using the first RF wireless communication link 450A or the second RF wireless communication link 450B). In certain examples, the RF wireless communication link 451 can include an optical, an acoustic, a magnetic, a body conductive, or other communication link.

In an example, a single first implantable antenna 420A or a single second implantable antenna 420B can be configured to operate at multiple RF wireless communication frequency ranges.

Figure 5:
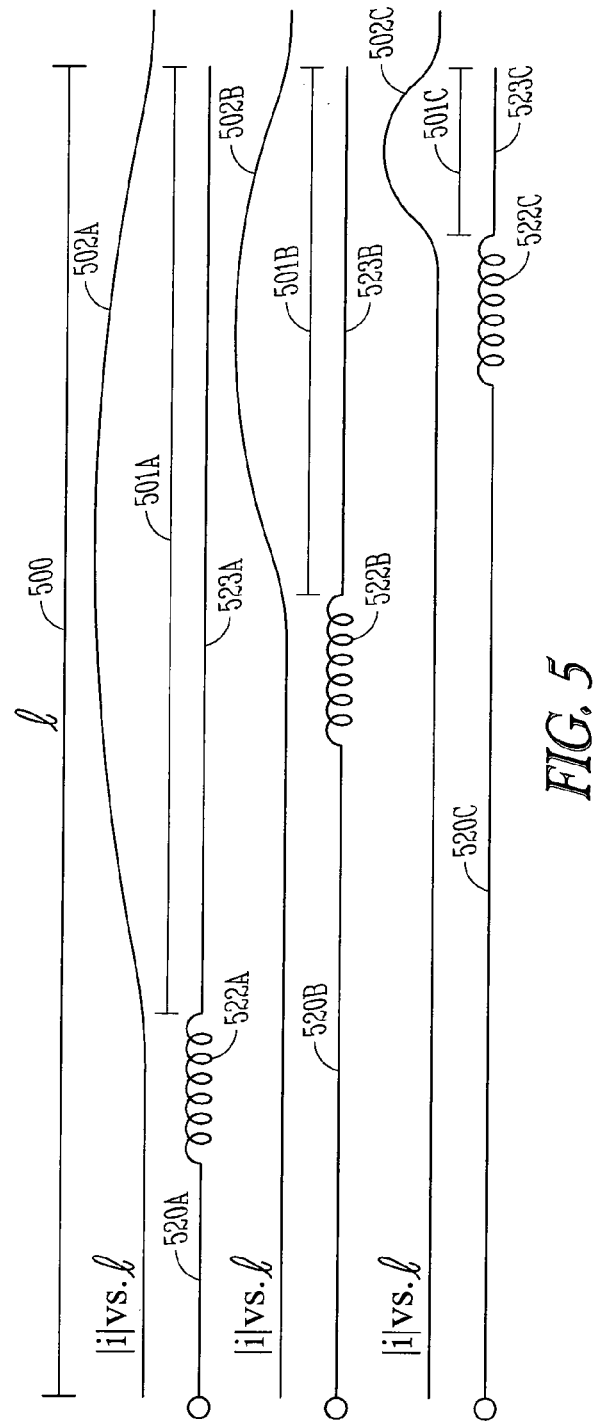
FIG. 5 illustrates generally examples of loaded implantable antenna configurations.

FIG. 5 illustrates generally examples of loaded implantable antenna configurations, including a base-loaded antenna 520A, a mid-loaded antenna 520B, and an end-loaded antenna 520C. In this example, each loaded implantable antenna configuration includes a coiled segment and a non-coiled segment, the base-loaded antenna 520A includes a coiled segment 522A and a non-coiled segment 523A, the mid-loaded antenna includes a coiled segment 522B and a non-coiled segment 523B, and the end-loaded antenna 520C includes a coiled segment 522C and a non-coiled segment 523C. In certain examples, a current profile can be adjusted for each loaded implantable antenna configuration, e.g., the base-loaded antenna 520A, the mid-loaded antenna 520B, or the end-loaded antenna 520C, using the location of the coiled segment, e.g., the coiled segment 522A, 522B, or 522C, along the length of the loaded implantable antenna. In this example, the base-loaded antenna 520A includes a current profile 502A, the mid-loaded antenna 520B includes a current profile 502B, and the end-loaded antenna 520C includes a current profile 502C. In these examples, the current profile 502A, 502B, or 502C illustrates generally a relative magnitude of an RF current along the loaded implantable antenna having a physical length "l" 500.

In certain examples, a physical arrangement of the non-coiled segment 523A, 523B, or 523C, with respect to the coiled segment 522A, 522B, or 522C, can alter the input impedance, a radiation efficiency, or a radiation pattern (e.g., the amount of radiation delivered in a particular direction away from the antenna, the amount of radiation received by the antenna from a particular direction, etc.) of the implantable loaded antenna configuration, e.g., the base-loaded antenna 520A, the mid-loaded antenna 520B, or the end-loaded antenna 520C.

In an example, the base-loaded antenna 520A can include a coiled segment, e.g., the coiled segment 522A, placed close in distance to a driving point of the antenna. In an example, a base-loaded antenna configuration can result in a current profile, e.g., a current profile 502A, concentrated along the non-coiled segment 523A. The current profile 502A illustrates generally the relative magnitude of an RF current at or near the base-loaded antenna 520A at a resonant frequency versus a total length 500 of the base-loaded antenna 520A. In an example, the current profile 502A can include a radiation region 501A. The radiation region 501A illustrates generally a portion of the base-loaded antenna 520A having the greatest radiation intensity based on the current profile 502A. In certain examples, the position of a coiled segment, e.g., the coiled segment 522A, along a loaded antenna, e.g., the base-loaded antenna 520A, can control or otherwise alter a radiation pattern of the loaded antenna.

In an example, the mid-loaded antenna 520B can include a coiled segment, e.g., the coiled segment 522B, placed approximately halfway along the length "l" 500 of the mid-loaded antenna 520B. In an example, a mid-loaded antenna configuration can result in a current profile, e.g., a current profile 502B, concentrated along the non-coiled segment 523B. In certain examples, the current profile 502B along the mid-loaded antenna 520B can include a radiation region 501B approximately coincident with non-coiled segment 523B and correspondingly shorter than a radiation region of an equivalent physical length base-loaded antenna configuration.

In an example, the end-loaded antenna 520C can include a coiled segment, e.g., the coiled segment 522C, placed farther in distance to the driving point of the antenna. In an example, an end-loaded antenna configuration can result in a current profile, e.g., a current profile 502C, concentrated along the non-coiled segment 523C. In certain examples, the current profile 523C along the end-loaded antenna 520C can include a radiation region 501C corresponding to the non-coiled segment 523C and correspondingly shorter than a radiation region of an equivalent physical length mid-loaded antenna configuration.

In certain examples, one or more of the current profiles of FIG. 5, e.g., the current profile 523A, 523B, or 523C, can be adjusted using one or more coiled segments, e.g., the coiled segment 522A, 522B, 522C, etc., or one or more configurations, geometries, geometry patters (such as a number of turns in a coiled segment, a pitch between the turns, a radius of the turns, a conductor cross section, etc.), or one or more other parameters. In an example, the one or more current profiles can be adjusted so that a peak current (e.g., a peak radiation) along the length (e.g., "l" 500) of the loaded implantable antenna configuration, e.g., the base-loaded antenna 520A, the mid-loaded antenna 520B, or the end-loaded antenna 520C, can occur before, or near the middle of, the one or more coiled segment of the loaded implantable antenna.

In other examples, a loaded implantable antenna, such as the base-loaded antenna 520A, the mid-loaded antenna 520B, or the end-loaded antenna 520C, can be designed, tuned, or otherwise configured to radiate omni-directionally (e.g., allowing a more uniform antenna performance or radiation with respect to the antenna orientation) using the geometric parameters of the one or more coiled segments of the loaded implantable antenna, such as the coiled segment 522A, 522B, or 522C. In an example, as the one or more geometric parameters of the one or more coiled segments the loaded implantable antenna decreases with respect to a wavelength, the range of directional radiation can increase.

In some examples, the one or more coiled segments of the loaded implantable antenna, such as the coiled segment 522A, 522B, or 522C, can be configured to provide an inductive load along the length "l" 500 of the loaded implantable antenna (e.g., similar to a discrete inductor placed along the length "l" 500 of the loaded implantable antenna). In certain examples, additional inductance can allow an antenna, such as the base-loaded antenna 520A, the mid-loaded antenna 520B, or the end-loaded antenna 520C, to radiate more efficiently than a similar, non-loaded, antenna (e.g., having a similar length). As such, the present inventor has recognized, among other things, that the addition of one or more coiled segments, such as the coiled segment 522A, 522B, or 522C, to an implantable antenna can reduce the physical length, e.g., "l" 500, of the antenna needed for a given radiation efficiency. In certain examples, the reduced physical length of the antenna can provide a space savings within an IMD. In certain examples, the radiation efficiency (e.g., "η") can be defined as the ratio of radiated electromagnetic energy versus the energy supplied to an implantable antenna by a connected telemetry circuit.

In an example, an inductive contribution from the one or more coiled segments of the loaded implantable antenna, such as the coiled segment 522A, 522B, or 522C, can provide improved radiation efficiency versus an antenna without the one or more coiled segments. When one or more coiled segments are included, the physical length "l" 500 of the antenna configuration can be less than a quarter of a wavelength at a desired operating frequency.

In an example, the one or more coiled segments, such as the coiled segment 522A, 522B, or 522C, can operate in a frequency selective manner (e.g., allowing an RF current to pass with a relatively low impedance at one range of frequencies versus blocking an RF current with a relatively high impedance in another range). In other examples, the one or more coiled segments can vary in inductance or capacitance with respect to frequency. In certain examples, a loaded implantable antenna, such as the base-loaded antenna 520A, the mid-loaded antenna 520B, or the end-loaded antenna 520C, can be configured with one or more coiled segments, such as the coiled segment 522A, 522B, or 522C, such that at a first specified range of operating frequencies, the loaded implantable antenna can radiate along one portion of its length "l" 500, such as region 501A, 501B, or 501C, and that at a second specified range of operating frequencies, the one or more coiled segment can provide a different impedance and the loaded implantable antenna can radiate along a different portion of its length "l" 500.

Figure 6:
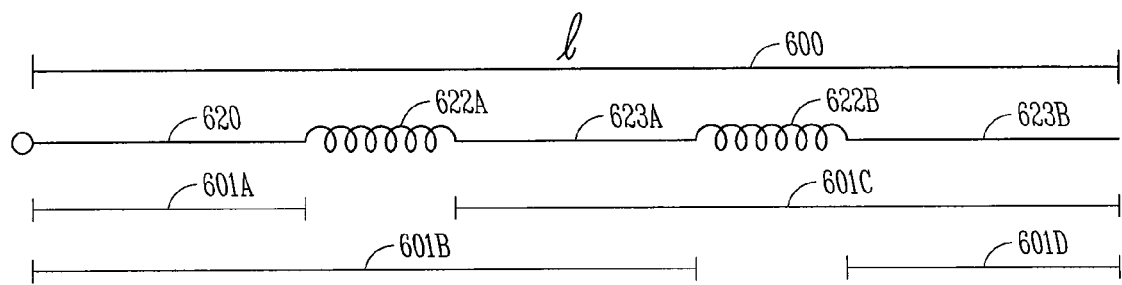
FIG. 6 illustrates generally an example of a loaded implantable antenna having at least two coiled segments.

FIG. 6 illustrates generally an example of a loaded implantable antenna 620 having at least two coiled segments, such as a first coiled segment 622A and a second coiled segment 622B. In an example, the loaded implantable antenna 620 can be configured to operate in multiple frequency ranges using the first coiled segment 622A and the second coiled segment 622B.

In some examples, the first coiled segment 622A and the second coiled segment 622B can be configured to provide a low impedance at a first specified operating frequency range to allow an RF current to flow to a non-coiled segment of the loaded implantable antenna 620, such as a first non-coiled segment 623A or a second non-coiled segment 623B. In an example, a radiation region, such as a third radiation region 601C or a fourth radiation region 601D, can represent one or more portions of the loaded implantable antenna 620 where the magnitude of an RF current passed through the first coiled segment 622A or the second coiled segment 622B can peak. In certain examples, the peak can result in a higher efficient radiation in the radiation region 601C or 601D.

In other examples, the first coiled segment 622A, the second coiled segment 622B, or a combination of both the first coiled segment 622A and the second coiled segment 622B can be configured to provide a high impedance at a second specified operating frequency range. In certain examples, the high impedance at the second specified operating frequency range can inhibit an RF current from flowing to a portion of the loaded implantable antenna 620, such as the second non-coiled segment 623B. In an example, the inhibiting the RF current can result in a radiation region, such as a second radiation region 601B, where radiation can occur more efficiently. Similarly, in some examples, the first coiled segment 622A can be configured to provide a high impedance at a third specified operating frequency range. In an example, the high impedance at the third specified operating frequency range can inhibit RF current from flowing through the first coiled segment 622A, resulting in more efficient radiation in a region, such as a first radiation region 601A.

Thus, the loaded implantable antenna 620 can be configured or tuned to operate (e.g., efficiently operate) at two or more desired ranges of operating frequencies by varying the physical arrangement (e.g., position, or geometric parameters) of the first coiled segment 622A or the second coiled segment 622B. In an example, the physical arrangement of the first coiled segment 622A or the second coiled segment 622B can result in the loaded implantable antenna 620, having a single physical length "l" 600 appearing electrically to have different electrical lengths corresponding to each of the two or more desired frequency ranges.

In some examples, the single physical length "l" 600 can be less than a quarter of a lowest specified operating wavelength. In certain examples, the lowest specified operating wavelength can correspond to a highest specified operating frequency. In an example, a loaded implantable antenna 620 can be configured to have a highest specified operating frequency of 2.5 GHz, corresponding to a wavelength in free space of approximately 0.1192 meters. One quarter of 0.1192 meters is approximately 0.0298 meters. Thus, in this example, the loaded implantable antenna 620 can have a physical length "l" 600 less than one quarter wavelength in free space, e.g., here, at 2.5 GHz, less than 0.298 meters long.

Generally, a desired length of an antenna changes roughly inversely proportionately with the relative dielectric constant of the medium surrounding the antenna. Thus, as the relative dielectric of a medium increases, the desired antenna length decreases. As such, in an example, if the loaded implantable antenna 620 is surrounded by a biological medium having a relative dielectric constant of 25, the desired length of the loaded implantable antenna 620 in the biological medium decreases by roughly the inverse square root of the relative dielectric constant, in this example, by 5. Thus, in this example, the physical length "l" 600 of the implantable loaded antenna 620 can be less than 0.006 meters long, and can be suitable for use in a compact IMD.

FIGS. 7A-7J illustrate generally examples of a system including an IMD housing (e.g., a first MD housing 710A, a second IMD housing 710B, etc.) and various implantable multi-frequency antenna configurations. In these examples, each IMD housing can be coupled to an IMD connector block (e.g., a first IMD connector block 721A, a second IMD connector block 721B, etc.).

Figure 7A:
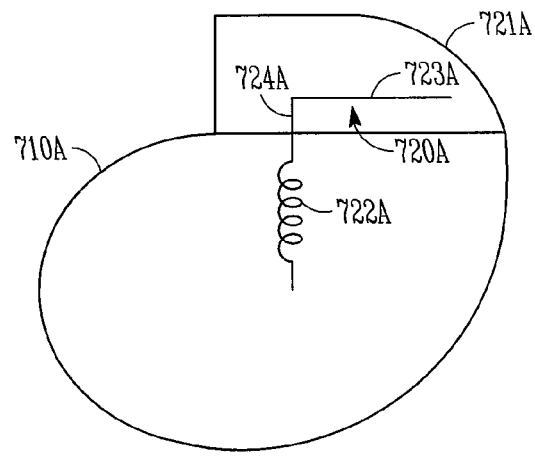
FIGS. 7A-7J illustrate generally examples of a system having an IMD housing and various implantable multi-frequency antenna configurations.

FIG. 7A illustrates generally a base loaded implantable antenna configuration including an IMD housing 710A, an IMD connector block 721A, and a base-loaded implantable antenna 720A, the base-loaded implantable antenna 720A including a coiled segment 722A, a non-coiled segment 723A, and a non-coiled feed segment 724A. In this example, the coiled segment 722A of the base-loaded implantable antenna 720A is internal to the IMD housing 710A. The base-loaded implantable antenna 720A penetrates the IMD housing 710A at the non-coiled feed segment 724A, and follows the base portion of the MD connector block 721A in proximity to the IMD housing 710A using the non-coiled segment 723A. In this example, the non-coiled portion 723A is contained within the MD connector block 721A. In some examples, a close proximity between the non-coiled segment 723A and the IMD housing 710A can enhance an RF coupling between the non-coiled segment 723A and the IMD housing 710A. The present inventor has recognized, among other things, that such coupling can reduce antenna radiation efficiency, but can also improve antenna impedance stability when the IMD housing 710A and the non-coiled segment 723A are surrounded by an implant media having a widely varying dielectric constant or conductivity (e.g., the dielectric properties of the connector block 721A can dominate at the cost of antenna radiation efficiency).

Figure 7B:
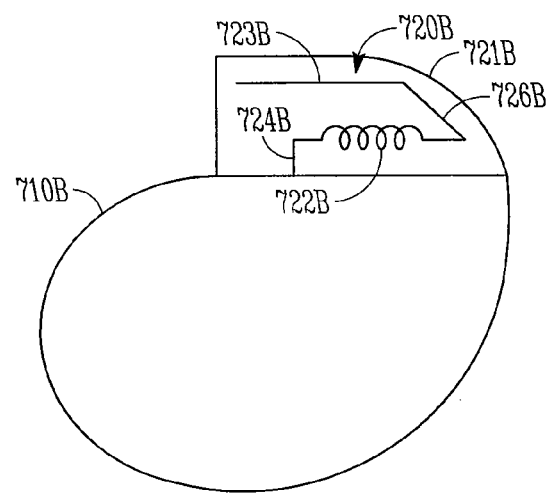

FIG. 7B illustrates generally a base-loaded implantable antenna configuration including an IMD housing 710B, an IMD connector block 721B, and a base-loaded implantable antenna 720B, the base-loaded implantable antenna 720B including a coiled segment 722B, a first non-coiled segment 723B, a non-coiled feed segment 724B, and a second non-coiled segment 726B. In this example, the non-coiled feed segment 724B penetrates the IMD housing 710B, and is coupled to the coiled segment 722B along the base portion of the IMD connector block 721B. In the example in FIG. 7B, the coiled segment 722B can be connected to the second non-coiled segment 726B via a sharp elbow. In certain examples, the second non-coiled segment 726B can follow a contour along a vertical edge of the IMD connector block 721B, and the second non-coiled segment 726B can be connected to the first non-coiled segment 723B along the top edge of the IMD connector block 721B. In this example, the first non-coiled segment 723B, the second non-coiled segment 726B, and the coiled segment 722B can be contained within the IMD connector block 721B.

In some examples, a close proximity between the non-coiled segment 723B and the edge of the IMD connector block 721B can result in enhanced radiation efficiency. However, the present inventor has recognized, among other things, that a tradeoff can exist wherein an antenna, e.g., the base-loaded implantable antenna 720B or other antenna, impedance or radiation efficiency can become more strongly dependent on variations in an implant medium dielectric constant or an implant medium conductivity when a portion of the antenna is configured such that a non-coiled segment is close to the edge of a connector block, e.g., the IMD connector block 721B.

Figure 7C:
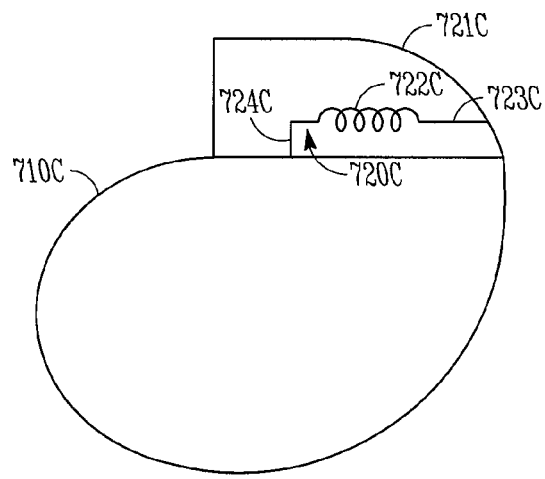

FIG. 7C illustrates generally a mid-loaded implantable antenna configuration including an IMD housing 710C, an IMD connector block 721C, and a mid-loaded implantable antenna 720C, the mid-loaded implantable antenna including a coiled segment 722C, a non-coiled segment 723C, and a non-coiled feed segment 724C. In this example, the non-coiled feed segment 724C penetrates the IMD housing 710C and is coupled to the coiled segment 722C along a base portion of the IMD connector block 721C. In the example of FIG. 7C, the non-coiled segment 723C can be coupled to the coiled segment 722C along the base portion of the connector block 721C. In an example, the non-coiled segment 723C and the coiled segment 722C can be contained within the IMD connector block 721C.

Figure 7D:
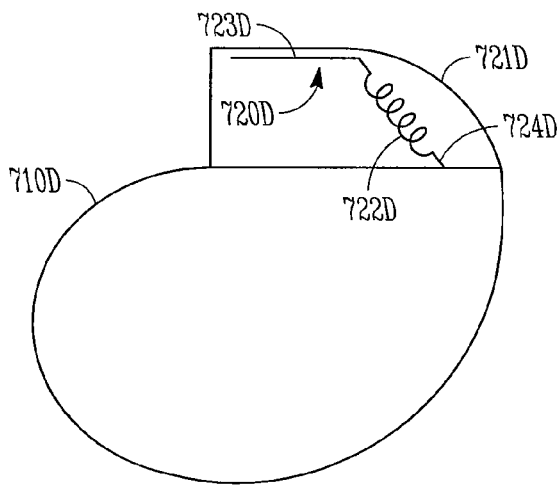

FIG. 7D illustrates generally a base-loaded implantable antenna configuration including an IMD housing 710D, an IMD connector block 721D, and a base-loaded implantable antenna 720D, the base-loaded implantable antenna 720D including a coiled segment 722D, a non-coiled segment 723D, and a non-coiled feed segment 724D. In this example, the non-coiled feed segment 724D penetrates the IMD housing 710D and is connected to the coiled segment 722D following a contour along a vertical edge of the connector block 721D. In certain examples, the feed non-coiled feed segment 724D can be coupled to a second non-coiled segment (not shown) before being connected to the coiled segment 722D. In the example of FIG. 7D, the coiled segment 722D can be connected to the non-coiled segment 723D configured to run along a top edge of the connector block 721D. In an example, the non-coiled segment 723D and the coiled segment 722D can be contained within the IMD connector block 721D.

Figure 7E:
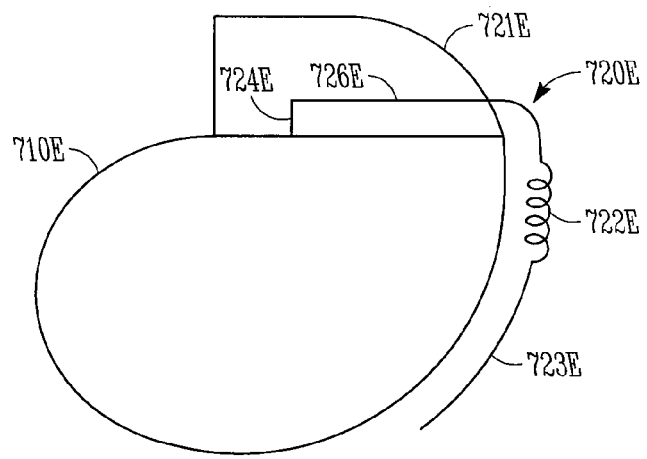

FIG. 7E illustrates generally a mid-loaded implantable antenna configuration including an IMD housing 710E, an IMD connector block 721E, and a mid-loaded implantable antenna 720E, the mid-loaded implantable antenna 720E including a coiled segment 722E, a first non-coiled segment 726E, a second non-coiled segment 723E, and a non-coiled feed segment 724E. In this example, the non-coiled feed segment 724E penetrates the IMD housing 710E and is connected to the first non-coiled segment 726E along a base portion of the connector block 721E. In an example, the first non-coiled segment 726E can be substantially contained within the IMD connector block 721E, but can penetrate the MD connector block 721D at an end opposite a feed point. In the example of FIG. 7E, the first non-coiled segment 726E can be connected to the coiled segment 722E. The coiled segment 722E can be configured to follow an exterior contour of the IMD housing 710E, and further can be configured to be connected or otherwise coupled to the second non-coiled segment 723E.

In certain examples, the second non-coiled segment 723E and the coiled segment 722E can be exposed directly to a termination medium surrounding the IMD housing 710E. In an example, this exposure can result in a significant variation in antenna radiation efficiency or impedance, depending on the dielectric or conductive characteristics of the implant medium surrounding the antenna versus air. However, the present inventor has recognized, among other things, that such an exposed configuration can also result in higher radiation efficiency due to a reduction of a loading effect by the MD housing 710E. In other examples, the second non-coiled segment 723E and the coiled segment 722E can be surrounded with a biocompatible dielectric film, such as, Poly-Ether-Ether-Ketone, Polyimide, or other biocompatible dielectric film or material. In certain examples, selected regions of the mid-loaded implantable antenna 720E outside of the IMD connector block 721E can be exposed to tissue.

In some examples, the second non-coiled segment 723E can be contained within a separate dielectric compartment to preserve a specified distance between the second non-coiled segment 723E and the IMD housing 710E. In an example, the dielectric compartment can be made from the same material as the IMD connector block 721E, such as a biocompatible polymer material.

Figure 7F:
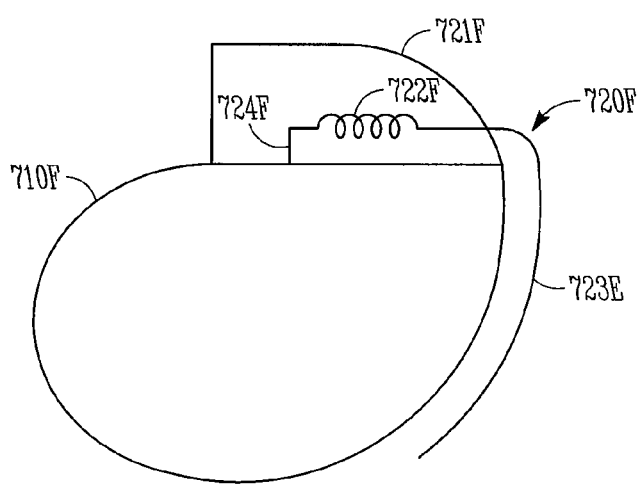

FIG. 7F illustrates generally a base-loaded implantable antenna configuration including an IMD housing 710F, an IMD connector block 721F, and a base-loaded implantable antenna 720F, the base loaded implantable antenna 720F including a coiled segment 722F, a non-coiled segment 723F, and a feed segment 724F. In an example, the feed segment 724F can include a coiled or a non-coiled feed segment. In this example, the feed segment 724F can penetrate the IMD housing 710F and is connected to the coiled segment 722F contained within the IMD connector block 721F. In an example, the coiled segment 722F can be connected to the non-coiled segment 723F, which can run along a base of the IMD connector block 721F. In certain examples, the non-coiled segment 723F can be partially contained within the connector block 721F, can penetrate the connector block 721F, or can follow an exterior contour of the housing 710F.

Figure 7G:
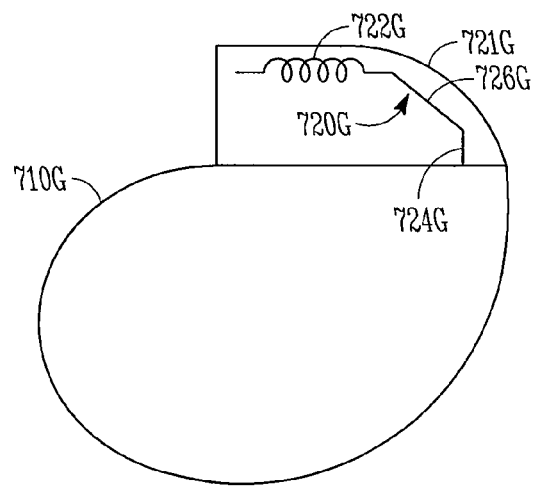

FIG. 7G illustrates generally an end-loaded implantable antenna configuration including an IMD housing 710G, an IMD connector block 721G, and an end-loaded implantable antenna 720G, the end-loaded implantable antenna 720G including a first non-coiled segment 726G, a coiled segment 722G, a second non-coiled segment 723G, and a feed segment 724G. In an example, the feed segment 724G penetrates the IMD housing 710G and is coupled to the first non-coiled segment 726G via a sharp bend at a corner of the IMD connector block 721G. In the example of FIG. 7G, the first non-coiled segment 726G follows a contour on a vertical edge of the IMD connector block 721G, and can form a sharp bend at the intersection of a vertical edge of the IMD connector block 721G and a top edge of the IMD connector block 721G. In certain examples, the coiled segment 722G can be connected to the first non-coiled segment 726G, and the coiled segment 722G can be connected to the second non-coiled segment 723G along a top edge of the IMD connector block 721G.

Figure 7H:
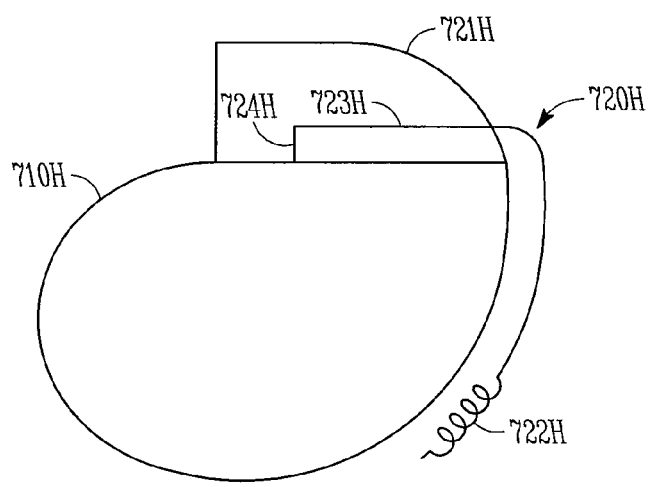

FIG. 7H illustrates generally an end-loaded implantable antenna configuration including an IMD housing 710H, an IMD connector block 721H, and an end-loaded implantable antenna configuration 720H including a non-coiled segment 723H, a coiled segment 722H, and a feed segment 724H. In an example, the feed segment 724H penetrates the IMD housing 710H and is connected to the non-coiled segment 723H, the non-coiled segment partially contained within the IM D connector block 721H. In certain examples, the coiled segment 722H can be connected to the non-coiled segment 723H at a far end of the end-loaded implantable antenna 720H.

Figure 7I:
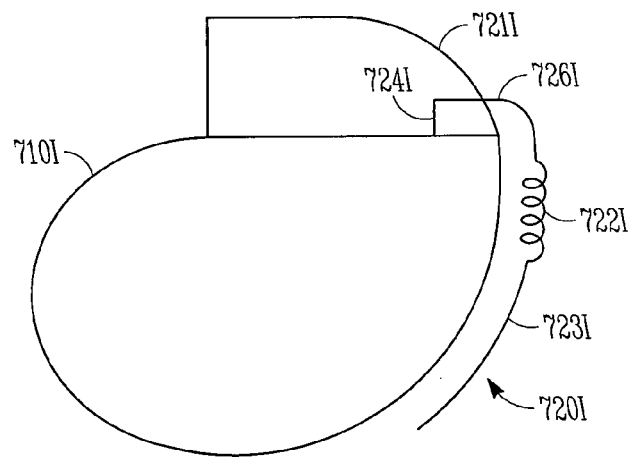

FIG. 7I illustrates generally a mid-loaded implantable antenna configuration including an IMD housing 710I, an IMD connector block 721I, and a mid-loaded implantable antenna 720I, the mid-loaded implantable antenna 720I including a first non-coiled segment 726I, a coiled segment 722I, a second non-coiled segment 723I, and a feed segment 724I. In an example, the feed segment 724I penetrates the IMD housing 710I at a feed point and is connected to the first non-coiled segment 726I. In an example, the first non-coiled segment 726I can penetrate the MD connector block 721I. In certain examples, the feed segment 724I can be connected to the coiled segment 722I, the coiled segment 722I located outside the IMD connector block 721I, and the coiled segment 722I can be connected to the second non-coiled segment 723I.

Figure 7J:
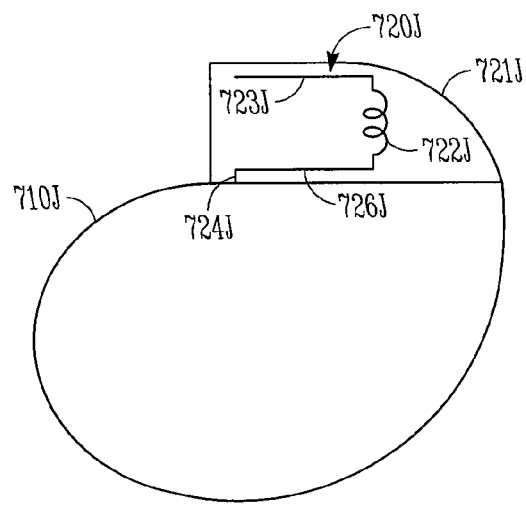

FIG. 7J illustrates generally a mid-loaded implantable antenna configuration including an IMD housing 710J, an IMD connector block 721J, and a mid-loaded implantable antenna 720J, the mid-loaded implantable antenna 720J including a first non-coiled segment 726J, a coiled segment 722J, a second non-coiled segment 721J, and a feed segment 724J. In an example, the feed segment 724J can penetrate the IMD housing 710J and can be connected to the first non-coiled segment 726J running along a lower portion of the IMD connector block 721J. In the example of FIG. 7J, the coiled segment 722J can be located along a vertical edge of the IMD connector block 721J and can be connected to the second non-coiled segment 723J located along a top edge of the IM D connector block 721J. In some examples, the length of at least one of the feed segment 724J, the first non-coiled segment 726J, the coiled segment 722J, or the second non-coiled segment 723J can be approximately equal.

In the examples of FIGS. 7A-7J, the length of one or more coiled segments, e.g., the coiled segment 722A, etc., can be equal to or shorter than the length of one or more non-coiled segments, e.g., the non-coiled segment 723A, etc. In some examples, one or more feed segments, e.g., the non-coiled feed segment 724A, etc., can penetrate an IMD housing, e.g., the IMD housing 710A, etc., through a top edge, where an IMD connector block, e.g., the IMD connector block 721A, etc., is mechanically or electrically coupled to the IMD housing. In some examples, the one or more feed segments can penetrate the IMD housing through a side of the IMD housing.

Figure 8:
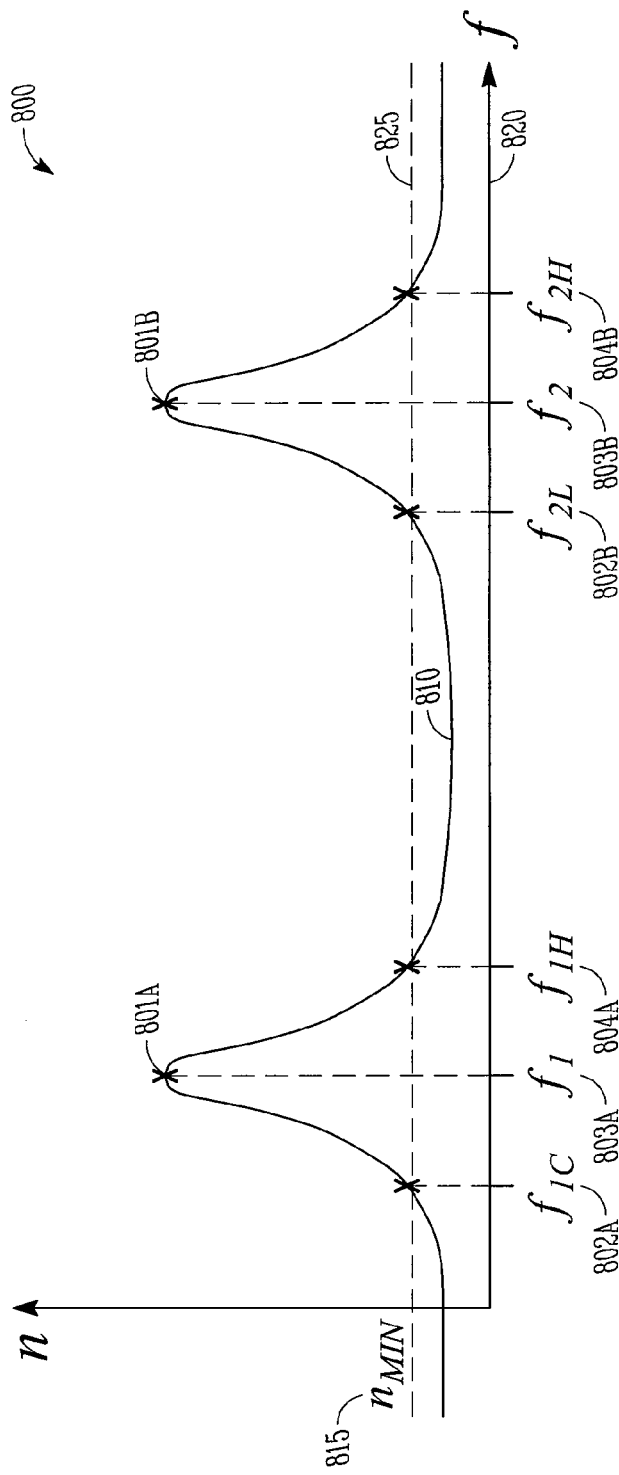
FIG. 8 illustrates generally an example of a relationship between an antenna radiation efficiency and frequency.

FIG. 8 illustrates generally an example of a relationship 800 between an antenna radiation efficiency 810 and frequency 820. On a vertical axis 805, the antenna radiation efficiency 810, ("η"), can be plotted versus frequency 820. In an example, the antenna radiation efficiency 810 can be provided for a multi-frequency antenna having two or more regions above specified minimum radiation efficiency 815, ("$\eta_{MIN}$"). In this example, a first operable range of frequencies can be specified by defining a first lower frequency limit 802A, $f_{1L}$, and a first upper frequency limit 804B, $f_{1H}$, at which an antenna radiation efficiency 810 is greater than or equal to a specified minimum radiation efficiency 815. A first mid-band frequency 803A, $f_1$, can be defined approximately where a first radiation efficiency peak 801A can occur.

Similarly, in the example of FIG. 8, a second operable range of frequencies can be specified by defining a second lower frequency limit 802B, $f_{2L}$, and a second upper frequency limit 804B, $f_{2H}$, at which an antenna radiation efficiency 810 is greater than or equal to a specified minimum radiation efficiency 815. A second mid-band frequency 803B, $f_2$, can be defined approximately where a first radiation efficiency peak 801B can occur.

In some examples, a first radiation efficiency peak 801A or a second radiation efficiency peak 801B can occur when the multi-frequency antenna is operated at or near a resonant frequency.

In an example, a multi-frequency antenna can be configured to operate over a first frequency range of approximately $f_{1L}=375$ MHz. and $f_{1H}=425$ MHz, and a first mid-band frequency 803A of approximately $f_1=400$ MHz. In this example, the multi-frequency antenna can be configured to operate over a second frequency range of approximately $f_{2L}=850$ MHz. and $f_{2H}=900$ MHz, and a second mid-band frequency 803B of approximately $f_2=875$ MHz.

In other examples, a multi-frequency antenna can be configured to operate over a first frequency range of approximately $f_{1L}=900$ MHz. and $f_{1H}=950$ MHz., and a first mid-band frequency 803A of approximately $f_1=925$ MHz. In this example, the multi-frequency antenna can be configured to operate over a second frequency range of approximately $f_{2L}=2.4$ GHz. and $f_{2H}=2.5$ GHz., and a second mid-band frequency 803A of approximately $f_2=2.45$ GHz.

In certain examples, a multi-frequency antenna can be configured to operate in at least two of:

(1) a Short Range Device (SRD) band range (e.g., 862-870 MHz.);

(2) a first Industrial-Scientific-Medical (ISM) band range (e.g., 902-928 MHz.);

(3) a second Industrial-Scientific-Medical (ISM) band range (e.g., 2.4-2.5 GHz.);

(4) a Medical Implant Communications Service (MICS) band range (e.g., 402-405 MHz.); or (5) one or more other frequency band ranges configured for communication between an IMD and one or more other implantable or external devices.

Figure 9:
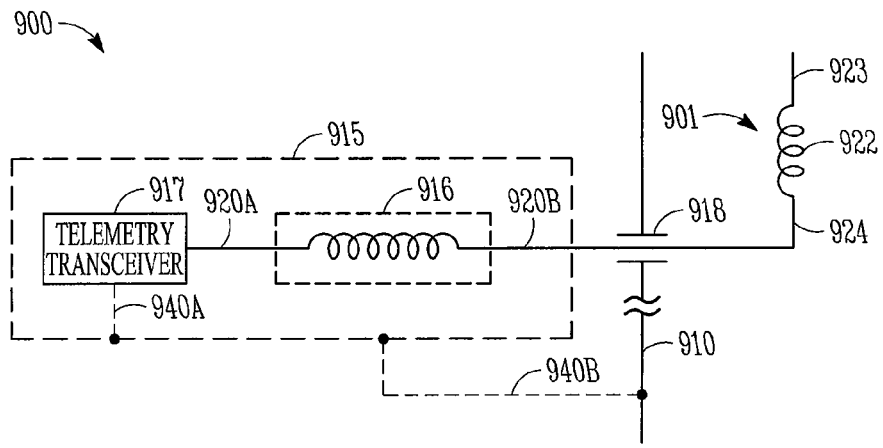
FIG. 9 illustrates generally an example of a system including a telemetry circuit coupled to an implantable antenna.

FIG. 9 illustrates generally an example of a system 900 including a telemetry circuit 915 coupled to an antenna 901. In certain examples, the telemetry circuit 915 can be partially or completely enclosed in a housing 910, such as an IMD housing.

In some examples, the housing 910 can be made of a conductive material, and the telemetry circuit 915 can be electrically connected using a second electrical connection 940B to the housing (e.g., an antenna RF current return path to a telemetry transceiver 917 can be provided using a first electrical connection 940A or the second electrical connection 940B).

In the example shown in FIG. 9, a second RF input/output line 920B for the telemetry circuit 915 can be electrically connected to a feed-through 918. The feed-through 918 can penetrate the housing 910 to drive a first non-coiled segment 924. In the example shown in FIG. 9, a first coiled segment 922 can be connected to the first non-coiled segment 924, and the first coiled segment 922 can be connected to a second non-coiled segment 923 to form, for example, a mid-loaded implantable antenna.

In an example, when the first coiled segment 922 is omitted from the antenna shown in FIG. 9, and a similar length non-coiled segment is substituted, the antenna can provide a capacitive load to the telemetry circuit 915 at the second RF input/output line 920B looking into the antenna 901 through the feed-through 918. In some examples, an impedance matching element 916 can be included to compensate for an excess inductance or capacitance of the antenna 901. In the example of the omitted first coiled segment 922, the impedance matching element 916 can include a discrete inductor. In the example of FIG. 9, the first coiled segment 922 can reduce the value of or eliminate the need for an impedance matching element 916 within the telemetry circuit 915.

In some examples, power transfer to the antenna 901 at a given frequency can be enhanced by providing a conjugate impedance match between a first RF input/output line 920A and the antenna 901. In an example, the antenna 901 can have a real portion of an input impedance looking into the antenna through the feed-through 918 of 50 Ohms. In this example, when the first coiled segment 922 is omitted from the antenna and a similar length non-coiled segment is substituted, the antenna can have an imaginary portion of an impedance of approximately −j20 Ohms (e.g., the antenna can present a capacitive load to the telemetry circuit 915).

In an example, to achieve a conjugate impedance match, neglecting the phase contribution of the first RF input/output line 920A and the second RF input/output line 920B, the impedance matching element 916 can be used to provide an inductive contribution to the output impedance of a telemetry transceiver 917 of approximately +j20 Ohms to approximately cancel out the capacitance of the antenna 901.

In another example, the first coiled segment 922 can be included in the antenna 901 (e.g., to provide inductive loading, as shown in FIG. 9), and can compensate for the antenna capacitance to provide an approximately real input impedance (e.g., without an imaginary component) looking into the antenna at the feed-through 918. In this example, the impedance matching element 916 can be omitted, or can be replaced with a purely resistive matching element 916 (e.g., a substantially resistive mismatch can exist between the antenna 901 and the output impedance of the telemetry transceiver 917).

In one example, when the antenna is operated at multiple frequencies, a matching element 916 can be used to provide an enhanced conjugate match at a first operating frequency range, and the impedance matching contribution from the first coiled segment 922 can be minimal in the first operating frequency range. Similarly, in an example, an impedance matching contribution from the matching element 916 can be minimal in a second operating frequency range, and the impedance matching contribution can from the first coiled segment 922 can be used to provide an enhanced conjugate match (e.g., if the matching element 916 is operated at its unity-power factor self-resonant frequency, it can appear as a resistive element rather than as a capacitive or an inductive component).

In an example, when the antenna is operated at multiple frequencies, the matching element 916 can be controllably switched out of the transmit and receive path between the first RF input/output line 920A and the second RF input/output line 920B. In certain examples, one or more values can be selected for the matching element 916 in order to provide an approximate conjugate match at more than one specified range of operating frequencies.

Figure 10:
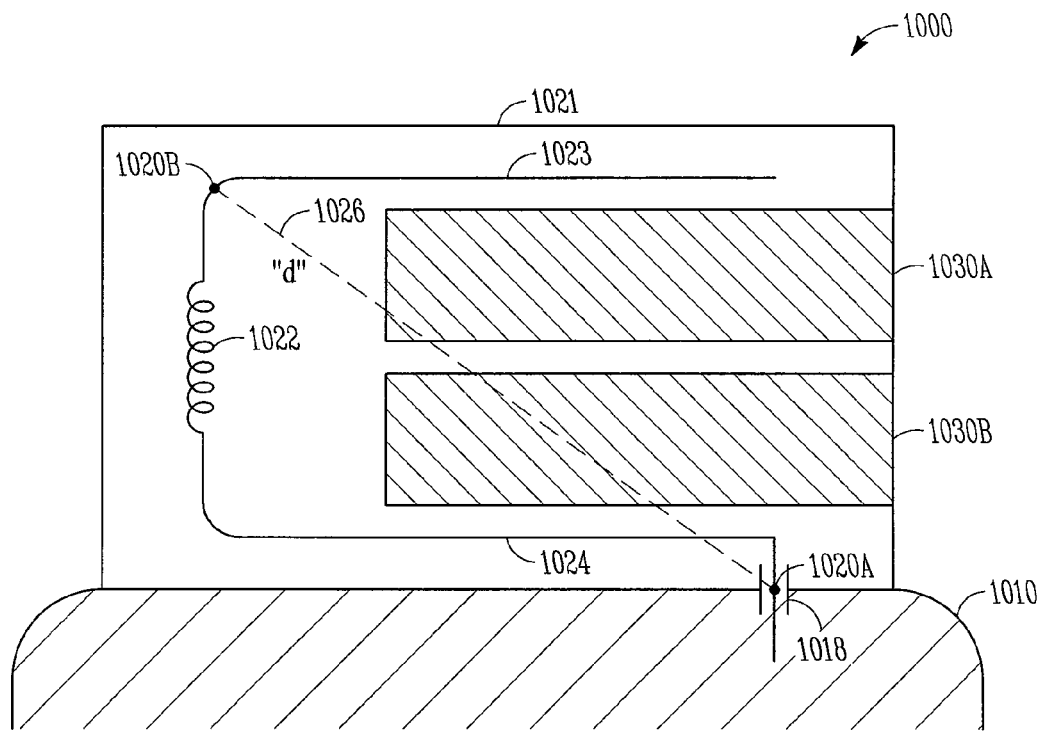
FIG. 10 illustrates generally an example of a system including a loaded antenna having a longest linear dimension "d."

FIG. 10 illustrates generally an example of a system 1000 including an antenna 1001 (e.g., a loaded multi-frequency antenna) having a longest linear dimension "d" 1026. In an example, the longest linear dimension 1026 can be determined by first identifying a base location 1020A and a distal location 1020B, the distal location 1020B including a location along the length of the antenna 1001 farthest away from the base location 1020A, and then, measuring the distance between the base location 1020A, here, at the antenna feed 1018, and the distal location 1020B.

In an example (similar to the example of FIG. 7J), a housing 1010 can be penetrated at a feed-through, e.g., the antenna feed 1018, by a first non-coiled segment 1024 running along a base of a connector block 1021. A first coiled segment 1022 can be connected to the first non-coiled segment 1024, and connected to a second non-coiled segment 1023 located along the top of the connector block 1021.

In this example, the antenna 1001 can use the volume inside the connector block 1021 more efficiently because the space occupied by a first lead connection 1030A and a second lead connection 1030B are not interfered with by the antenna 1001. In an example, an IMD can require a certain connector block 1021 volume to accommodate the first or second lead connections 1030A, 1030B, but can be expanded slightly above the first lead connection 1030A in order to accommodate the second non-coiled segment 1023 along the top edge of the connector block 1021.

In certain examples, expanding the size of the connector block 1021 can reduce or eliminate the need for a separate dielectric housing for a portion of the antenna. In some examples, the orientation of the first coiled segment 1022 can be vertical, horizontal, diagonal, or following a curved path to avoid interconnections between the first and second lead connections 1030A, 1030B, or other circuitry contained within the housing 1010. In an example, the orientation, geometry, or other parameter of the first coiled segment 1022, the first non-coiled segment 1024, or the second non-coiled segment 1023 can be specified to achieve a desired antenna impedance or heightened radiation efficiency over one or more ranges of operating frequencies, similar to the discussion in FIG. 5 or 7A-J.

In some examples, similar to those discussed in FIG. 5, 6, 7, 9, or 10, the first coiled segment 1022, or other coiled segments, can be formed or made from a wire wound and formed to achieve a desired antenna shape, from a ribbon-shaped conductor, or from one or more other conductors.

In other examples, similar to those discussed in FIG. 5, 6, 7, 9 or 10, the antenna 1001 can be formed or made from a wire wound and formed to achieve a desired antenna shape, from a ribbon-shaped conductor (e.g., a rectangular or other cross section, etc.), or from one or more other conductors. In some examples, the implantable antenna can be realized on a planar structure (e.g., a printed circuit board, or an IMD housing).

In certain examples, the conductor used for one or more segment of the antenna 1001 can include platinum, iridium, gold, silver, copper, tin, aluminum, steel, a combination of metals, or one or more other conductors. In an example, if one or more portions of the antenna 1001 or an implantable telemetry circuit are in contact with tissue, a biocompatible conductive material can be used, such as an alloy of platinum and iridium, etc.

In some examples, loading or multi-frequency operation can be achieved by inserting one or more coiled segments in-line with one or more other antenna type (e.g., a helical antenna, a spiral antenna, a fractal antenna, a serpentine antenna, an inverted-F antenna, a patch antenna, or other antenna type). In some examples, a coiled segment can be realized on a planar structure, such as a printed circuit board, and can occupy one or more metal layers separated by one or more dielectric slabs.

FIG. 11A illustrates generally an example of a process 1100 including wirelessly transferring information using an implantable antenna. At 1105, information can be wirelessly electromagnetically transferred at a first specified operating frequency range and a second specified operating frequency range using an implantable antenna. In an example, the implantable antenna can include any antenna sized and shaped or otherwise configured to be implanted in a human or animal body, such as an implantable antenna 120 or other implantable antenna.

In an example, the first specified operating frequency range and the second specified operating frequency range can be provided at least in part by a physical orientation of the implantable antenna. In certain examples, the implantable antenna can include a first non-coiled segment and a first coiled segment. In an example, the first non-coiled segment can be attached or otherwise coupled to the first coiled segment. In an example, the first specified operating frequency range and the second specified operating frequency range can be provided at least in part by the physical arrangement of the first coiled segment with respect to the first non-coiled segment.

In other examples, the implantable antenna can include one or more other coiled or non-coiled sections, such as a second coiled section, a second non-coiled section, etc. Accordingly, the first specified operating frequency range and the second specified operating frequency range can be provided at least in part by the physical arrangement of at least one of the first coiled segment, the first non-coiled segment, the second coiled segment, the second non-coiled segment, or one or more other coiled or non-coiled segments.

FIG. 11B illustrates generally an example of a process 1101 including driving an implantable antenna using an implantable telemetry circuit and wirelessly transferring information electromagnetically using at least one of a first or second specified operating frequency range.

At 1110, an implantable antenna can be driven using an implantable telemetry circuit. In an example, the implantable telemetry circuit can include any telemetry circuit sized and shaped or otherwise configured to be implanted in a human or animal body, such as an implantable telemetry circuit 115 or other implantable telemetry circuit.

In an example, the implantable telemetry circuit can be contained within an implantable conductive or non-conductive housing, such as an implantable assembly or other housing sized and shaped or otherwise configured to be implantable in a human or animal body. In certain examples, the implantable antenna can be located outside of the implantable housing.

At 1115, information can be wirelessly electromagnetically transferred between the implantable antenna and an external telemetry module antenna using at least one of a first specified operating frequency range or a second specified operating frequency range.

FIG. 12 illustrates generally an example of a comparison 1200 between a normalized first radiation pattern 1210 in a plane of an antenna with a coiled segment versus a similar second radiation pattern 1220 of an antenna without a coiled segment. In an example, the plane can be defined by two perpendicular axes, a first axis 1201A and a second axis 1201B. In this example, an outermost ring 1205A can represent a 0 dB value corresponding to a radiation maximum of an antenna (e.g., a location on the plot showing 0 dB corresponds to a direction where the highest antenna radiation occurs). A first inner ring 1205B and a second inner ring 1205C can represent, for example, −10 dB and −20 dB relative power levels, respectively.

In an example, an IMD including an implantable antenna can exhibit a cardioid-shaped radiation pattern, such as the first radiation pattern 1210 or the second radiation pattern 1220, in a plane normal to a long axis of the implantable antenna. As the antenna follows a contour of a conductive IMD housing, a shadow region of reduced radiated power can occur (e.g., the dimple or "null" area shown in the first radiation pattern 1210 or the second radiation pattern 1220). As an antenna is physically arranged further away from a conductive IMD housing, the housing can cause less of a shadow effect.

In certain examples, omni-directional operation can be desired to improve the reliability of RF wireless communication with an MD (e.g., to prevent communication drop-outs due to device orientation, dead spots, etc.). Omni-directionality can be characterized using an antenna directivity parameter. Directivity, D, can be defined as the ratio of the peak radiated power in the direction of maximum radiation over the average radiated power over all directions. In certain examples, the omni-directional antenna can exhibit 0 dB directivity (e.g., a one-to-one ratio between the peak radiated power and the average radiated power).

In an example, the average power corresponding to the second radiation pattern 1220 can be less than the average power corresponding to the first radiation pattern 1210 (since the area occupied by pattern 1210 encompasses the area occupied by pattern 1220). Therefore, in this example, the directivity corresponding to the second radiation pattern 1220 can be greater than the directivity corresponding to the first radiation pattern 1210. As such, the antenna having the coil segment can exhibit a more omni-directional pattern, such as the second radiation pattern 1220, or generally, a more uniform radiation in all directions.

In certain examples, more than one physical mechanism can decrease the directivity of an antenna having a coiled segment, and improve the uniformity of the associated radiation pattern. For example, the coil segment itself can contribute to radiation, and the majority of a coil winding can be in a plane perpendicular (e.g., normal) to a long axis of the antenna. This radiation can be called "non-boresight" radiation. In an example, non-boresight radiation can result when one or more geometry patterns of the coil segment, such as coil pitch, turn radius conductor cross section, etc., are smaller than a wavelength (e.g., much smaller than the wavelength).

In an example, the coil segment can also allow or enable a non-coiled segment of an antenna to radiate more efficiently, and as shown in FIG. 10, multiple non-coiled segments can radiate together from different locations within, for example, a connector block on an IMD (e.g., more of the physical length of the antenna can be used to radiate energy in multiple axes, and at multiple locations).

In some examples, an implantable telemetry circuit can be configured as a transmitter, or a receiver, or both. Generally, the principles described in connection with bi-directional wireless information transfer between an implantable antenna and another wireless device can also apply to unidirectional wireless information transfer. According to a physical principal of reciprocity, antenna behavior can be generally reciprocal (e.g., an antenna physically arranged as a transmitting antenna can also act as a receiving antenna having similar characteristics).

Other Examples

In an example, similar to the examples of FIG. 7, a feed line near an IMD housing can bring an RF connection to the back of a header, the header coupled to the IMD housing. In this example, the feed line, because it is near the IMD housing, can act as a micro-strip. In an example, a first segment can rise near vertically. In this example, the first segment can be placed in one axis (e.g., the z axis) covering, for example, a horizontal plane of radiation. In an example, the first segment, at the top of the header, can be coupled to a coiled segment. In certain examples, this location can represent or be selected as a location in the header having free or unoccupied space. In a mid-loaded design, a second segment can be coupled to the coiled segment, and can run across the top of the header in a second axis that is nearing perpendicular to the first. In an example, this location can yield the longest straight length for the segment. In an example, the second segment can be placed in one axis (e.g., the x axis) covering, for example, a vertical plane of radiation. In this example, the header can be enlarged slightly to house the new antenna, but, in certain examples, no other extra antenna structure can be needed in, on, or outside of the device (e.g., outside of the IMD housing, outside of the header, etc.).

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventor also contemplates examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B,""B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
an implantable telemetry circuit;
an implantable antenna electrically connected to the implantable telemetry circuit, the implantable antenna comprising:
a first non-coil segment having a proximal end and a distal end, wherein the proximal end is connected to the implantable telemetry circuit; and
a first coil having a proximal end and a distal end, wherein the proximal end is attached to the distal end of the first non-coil segment, and wherein the first coil comprises a continuous series of contiguous turns disposed about a first longitudinal axis; and
a second non-coil segment attached to the distal end of the first coil; and
wherein the implantable antenna is configured to wirelessly transfer information electromagnetically using a first specified operating frequency range and a second specified operating frequency range, wherein the first specified frequency range is established by a first resonant frequency and the different second specified operating frequency is established by a different second resonant frequency, and wherein the first specified operating frequency range and the second specified operating frequency range are provided at least in part by a physical arrangement of the first coil with respect to the first non-coil segment and the second non-coil segment;
an implantable housing sized and shaped for implant within a human or animal body, the implantable housing comprising a conductive material and containing at least a portion of the implantable telemetry circuit, wherein the conductive material is electrically connected to the implantable telemetry circuit;
a first implantable dielectric compartment sized and shaped for implant within a human or animal body, the first implantable dielectric compartment containing at least a portion of the first non-coil segment of the implantable antenna, and wherein the first implantable dielectric compartment is coupled to the housing; and
a second implantable dielectric compartment sized and shaped for implant within a human or animal body, the second implantable dielectric compartment containing the first coil of the implantable antenna, wherein the second implantable dielectric compartment is coupled to the housing, and wherein the first coil is configured to follow an exterior contour of the implantable housing.

2. The system of claim 1, wherein a first mid-band frequency, centered in the first specified operating frequency range, is offset from a second mid-band frequency, centered in the second operating frequency range, by at least an octave.

3. The system of claim 2, wherein the first and second specified operating frequency ranges are selected from a list including at least one of:
(1) a Medical Implant Communications Service (MICS) band range extending from approximately 402 MHz. to approximately 405 MHz.;
(2) a Short Range Device (SRD) band range extending from approximately 862 MHz. to approximately 870 MHz.;
(3) a first Industrial-Scientific-Medical (ISM) band range extending from approximately 902 MHz. to approximately 928 MHz.; or
(4) a second ISM band range extending from approximately 2400 MHz. to approximately 2500 MHz.

4. The system of claim 1, wherein an entire length of the implantable antenna is less than or equal to a quarter of a longest specified operating wavelength of the implantable antenna in a biological medium.

5. The system of claim 1, wherein the physical arrangement of the first coil with respect to the first non-coil segment is configured to provide an input impedance approximating a conjugate match to an output impedance of the implantable telemetry circuit for at least one of the first and second operating frequency ranges when the implantable antenna is implanted in a biological medium.

6. The system of claim 5, wherein the first coil is configured to inductively load the implantable telemetry circuit.

7. The system of claim 1, comprising:
an external telemetry module comprising:
an external antenna; and
an external telemetry circuit electrically connected to the external antenna;
wherein the implantable antenna and the external antenna are wirelessly coupled; and
wherein the external antenna is configured to wirelessly transfer information electromagnetically between the implantable medical assembly and the external telemetry module using at least one of the first or second specified operating frequency ranges.

8. The system of claim 1, wherein the implantable antenna comprises a biocompatible conductive material.

9. The system of claim 8, wherein at least a portion of the implantable antenna is configured to be exposed to tissue when the implantable antenna is implanted in a biological medium.

10. A method, comprising:
providing an implantable housing sized and shaped for implant within a human or animal body, the implantable housing comprising a conductive material and containing at least a portion of an implantable telemetry circuit, wherein the conductive material is electrically connected to the implantable telemetry circuit;
providing a first implantable dielectric compartment sized and shaped for implant within a human or animal body, wherein the first implantable dielectric compartment is coupled to the housing;
providing a second implantable dielectric compartment sized and shaped for implant within a human or animal body, wherein the second implantable dielectric compartment is coupled to the housing;
wirelessly transferring information electromagnetically at a first specified operating frequency range and at a second specified operating frequency range using an implantable antenna, the implantable antenna comprising:
a first non-coil segment having a proximal end and a distal end, wherein the proximal end is connected to the implantable telemetry circuit; and
a first coil having a proximal end and a distal end, wherein the proximal end is attached to the distal end of the first non-coil segment, wherein the first coil comprises a continuous series of contiguous turns disposed about a first longitudinal axis; and
a second non-coil segment attached to the distal end of the first coil; and
wherein the first specified operating frequency range and the second specified operating frequency range are provided at least in part by a physical arrangement of the first coil with respect to the first non-coil segment and the second non-coil segment;

wherein the first specified operating frequency range is established by a first resonant frequency and the second specified operating frequency is established by a different second resonant frequency, wherein the first implantable dielectric compartment contains at least a portion of the first non-coil segment of the implantable antenna, and wherein the second implantable dielectric compartment contains the first coil of the implantable antenna, and wherein the first coil is configured to follow an exterior contour of the implantable housing.

11. The method of claim 10, wherein the wirelessly transferring information electromagnetically includes using the first specified operating frequency range having a first midband frequency and the second specified operating frequency range having a second mid-band frequency, and wherein the first mid-band frequency is offset from the second mid-band frequency by at least an octave.

12. The method of claim 10, comprising substantially matching a conjugate impedance of the implantable antenna in a biological medium using the implantable telemetry circuit.

13. The method of claim 12, wherein the substantially matching includes inductively loading the implantable telemetry circuit using the first coil.

14. The method of claim 10, comprising:

driving the implantable antenna using the implantable telemetry circuit; and wherein the wirelessly transferring information electromagnetically includes wirelessly transferring information electromagnetically between the implantable antenna and an external telemetry module antenna using at least one of the first specified operating frequency range or the second specified operating frequency range.

15. The method of claim 10, wherein the implantable antenna comprises a biocompatible conductive material.

16. The method of claim 15, wherein at least a portion of the implantable antenna is configured to be exposed to tissue when the implantable antenna is implanted in a biological medium.

* * * * *